United States Patent
Schraga

(10) Patent No.: US 9,282,918 B2
(45) Date of Patent: Mar. 15, 2016

(54) MULTI-LANCET UNIT, METHOD AND LANCET DEVICE USING THE MULTI-LANCET UNIT, AND METHOD OF ASSEMBLING AND/OR MAKING THE MULTI-LANCET UNIT

(75) Inventor: Steven Schraga, Surfside, FL (US)

(73) Assignee: STAT MEDICAL DEVICES, INC., North Miami Beach, FL (US)

( * ) Notice: Subject to any disclaimer, the term of this patent is extended or adjusted under 35 U.S.C. 154(b) by 2845 days.

(21) Appl. No.: 11/428,207

(22) Filed: Jun. 30, 2006

(65) Prior Publication Data

US 2006/0241668 A1 Oct. 26, 2006

Related U.S. Application Data

(63) Continuation-in-part of application No. 11/044,008, filed on Jan. 28, 2005.

(51) Int. Cl.
| | |
|---|---|
| *A61B 17/32* | (2006.01) |
| *A61B 5/15* | (2006.01) |
| *A61B 5/151* | (2006.01) |
| *A61M 5/00* | (2006.01) |

(52) U.S. Cl.
CPC ........... *A61B 5/1411* (2013.01); *A61B 5/15146* (2013.01); *A61M 5/008* (2013.01)

(58) Field of Classification Search
USPC ............................ 604/191; 606/181, 182, 183
See application file for complete search history.

(56) References Cited

U.S. PATENT DOCUMENTS

| | | | |
|---|---|---|---|
| 676,678 A | 6/1901 | Ellifrits | |
| 1,135,465 A | 4/1915 | Pollock | |
| 2,848,809 A | 2/1956 | Crowder | |
| 2,823,677 A | 2/1958 | Hein, Jr. | |
| 3,030,959 A * | 4/1962 | Grunert | 606/182 |
| 3,589,213 A | 6/1971 | Gourley | |
| 3,760,809 A | 9/1973 | Campbell | |
| 4,064,871 A | 12/1977 | Reno | |
| 4,139,011 A | 2/1979 | Benoit et al. | |
| 4,157,086 A | 6/1979 | Maiorano et al. | |
| 4,203,446 A | 5/1980 | Höfert et al. | |

(Continued)

FOREIGN PATENT DOCUMENTS

| | | |
|---|---|---|
| CA | 523078 | 3/1956 |
| EP | 0061102 | 9/1982 |

(Continued)

OTHER PUBLICATIONS

Chinese Office Action issued in counterpart Chinese App. 2006800033403.

(Continued)

*Primary Examiner* — Kathleen Holwerda
*Assistant Examiner* — Sarah Simpson
(74) *Attorney, Agent, or Firm* — Greenblum & Bernstein, P.L.C.

(57) ABSTRACT

Multi-lancet unit for a lancet device. The unit includes a plurality of lancets arranged in a row. Each lancet has a front ends a needle which extends from the front end, and a rear end. The front end of at least one of the plurality lancets is removably connected to the rear end of another of the plurality of lancets. The lancet device utilizes the multi-lancet unit and includes a body and a holding member which supports the multi-lancet unit. This Abstract is not intended to define the invention disclosed in the specification, nor intended to limit the scope of the invention in any way.

33 Claims, 39 Drawing Sheets

(56) References Cited

U.S. PATENT DOCUMENTS

| | | |
|---|---|---|
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirley et al. |
| 4,553,541 A | 11/1985 | Burns |
| 4,628,929 A | 12/1986 | Intengan et al. |
| 4,643,189 A | 2/1987 | Mintz |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |
| 4,976,724 A | 12/1990 | Nieto et al. |
| 4,990,154 A | 2/1991 | Brown et al. |
| 5,035,704 A | 7/1991 | Lambert et al. |
| 5,074,872 A | 12/1991 | Brown et al. |
| 5,133,730 A | 7/1992 | Biro et al. |
| 5,147,375 A | 9/1992 | Sullivan et al. |
| 5,201,324 A | 4/1993 | Swierczek |
| 5,212,879 A | 5/1993 | Biro et al. |
| 5,269,799 A | 12/1993 | Daniel |
| 5,282,822 A | 2/1994 | Macors et al. |
| 5,304,193 A | 4/1994 | Zhadanov |
| 5,314,441 A | 5/1994 | Cusack et al. |
| 5,318,584 A | 6/1994 | Lange et al. |
| 5,324,303 A | 6/1994 | Strong et al. |
| 5,350,392 A | 9/1994 | Purcell et al. |
| 5,356,420 A | 10/1994 | Czernecki et al. |
| 5,366,470 A | 11/1994 | Ramel |
| 5,368,047 A | 11/1994 | Suzuki et al. |
| 5,395,388 A | 3/1995 | Schraga |
| 5,423,847 A | 6/1995 | Strong et al. |
| 5,439,473 A | 8/1995 | Jorgensen |
| 5,454,828 A | 10/1995 | Schraga |
| 5,464,418 A | 11/1995 | Schraga |
| 5,476,101 A | 12/1995 | Schramm et al. |
| 5,487,748 A | 1/1996 | Marshall et al. |
| 5,509,345 A | 4/1996 | Cyktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 5/1997 | Schraga |
| 5,628,765 A | 5/1997 | Morita |
| 5,643,306 A | 7/1997 | Schraga |
| 5,662,672 A | 9/1997 | Pambianchi et al. |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange et al. |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brenneman et al. |
| 5,971,941 A | 10/1999 | Simons et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,086,545 A | 7/2000 | Roe et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,161,976 A | 12/2000 | Liu |
| 6,168,606 B1 | 1/2001 | Levin et al. |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 | 3/2001 | LeVaughn et al. |
| 6,210,420 B1 | 4/2001 | Mauze et al. |
| 6,221,089 B1 | 4/2001 | Mawhirt |
| 6,228,100 B1 | 5/2001 | Schraga |
| 6,258,112 B1 | 7/2001 | Schraga |
| 6,283,982 B1 | 9/2001 | Levaughn et al. |
| 6,306,152 B1 | 10/2001 | Verdonk et al. |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig |
| 6,395,495 B1 | 5/2002 | Motagnier et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schraga |
| 6,540,762 B1 | 4/2003 | Bertling |
| 6,558,402 B1 | 5/2003 | Chelak et al. |
| 6,645,219 B2 | 11/2003 | Roe |
| 7,087,068 B1 | 8/2006 | Marshall et al. |
| 7,175,641 B1 | 2/2007 | Schraga |
| 7,226,228 B1* | 6/2007 | San Miguel ............... 401/57 |
| 7,299,081 B2 | 11/2007 | Mace et al. |
| 7,311,718 B2 | 12/2007 | Schraga |
| 2001/0027327 A1 | 10/2001 | Schraga |
| 2001/0039387 A1 | 11/2001 | Rutynowski et al. |
| 2001/0053891 A1 | 12/2001 | Ackley |
| 2002/0077650 A1 | 6/2002 | Schraga |
| 2002/0169470 A1 | 11/2002 | Kuhr et al. |
| 2003/0050573 A1 | 3/2003 | Kuhr et al. |
| 2003/0050655 A1 | 3/2003 | Roe |
| 2003/0050656 A1 | 3/2003 | Schraga |
| 2003/0083686 A1 | 5/2003 | Freeman et al. |
| 2004/0092995 A1 | 5/2004 | Boecker et al. |
| 2004/0193202 A1 | 9/2004 | Allen |
| 2004/0230216 A1 | 11/2004 | LeVaughn et al. |
| 2004/0236362 A1* | 11/2004 | Shraga ............... 606/181 |
| 2004/0260325 A1 | 12/2004 | Kuhr et al. |
| 2005/0021066 A1 | 1/2005 | Kuhr et al. |
| 2005/0118071 A1 | 6/2005 | Sacherer |
| 2005/0234495 A1 | 10/2005 | Schraga |
| 2005/0277850 A1 | 12/2005 | Mace et al. |
| 2006/0173478 A1 | 8/2006 | Schraga |
| 2006/0224172 A1 | 10/2006 | LeVaughn et al. |
| 2008/0033468 A1 | 2/2008 | Lathrop et al. |
| 2008/0039885 A1 | 2/2008 | Purcell |

FOREIGN PATENT DOCUMENTS

| | | |
|---|---|---|
| EP | 0137975 | 10/1990 |
| EP | 0189117 | 3/1991 |
| EP | 0 838 195 | 4/1998 |
| EP | 0885590 | 12/1998 |
| EP | 0904731 | 3/1999 |
| EP | 1074219 | 2/2001 |
| EP | 1 142 534 | 10/2001 |
| FR | 1126718 | 11/1956 |
| FR | 2 797 579 | 2/2001 |
| KR | 10-2001-0020623 | 3/2001 |

(56) References Cited

FOREIGN PATENT DOCUMENTS

| WO | WO 93/19671 | 10/1993 |
| WO | WO 99/63897 | 12/1999 |
| WO | WO 03/022130 | 3/2003 |
| WO | 03/083469 | 10/2003 |
| WO | WO 2005/018710 | 3/2005 |

OTHER PUBLICATIONS

Sutor et al., "Bleeding from Standardized Skin Puncture; Automated Technic for Recording Time, Intensity, and Pattern of Bleeding", *A.J.C.P.*, vol. 55, pp. 541-549 (May 1971).

Australian Office Action dated Oct. 18, 2010 that issued with respect to patent family member Australian Patent Application No. 2006-211171.

\* cited by examiner

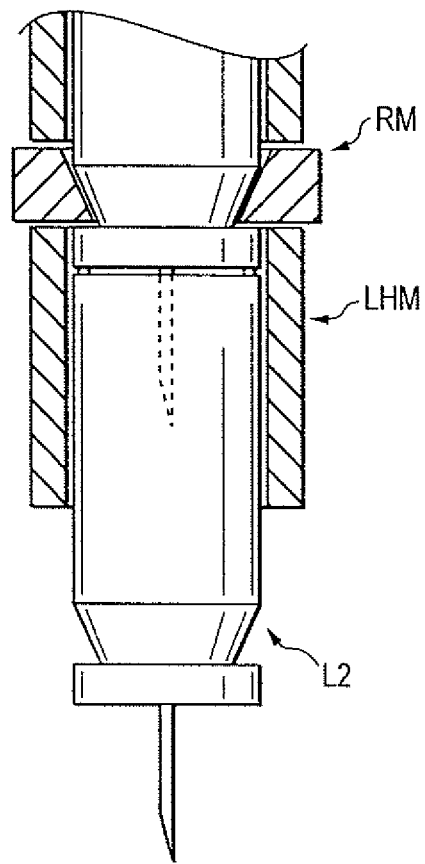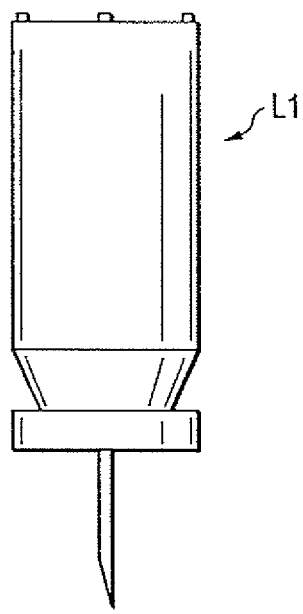
FIG. 13

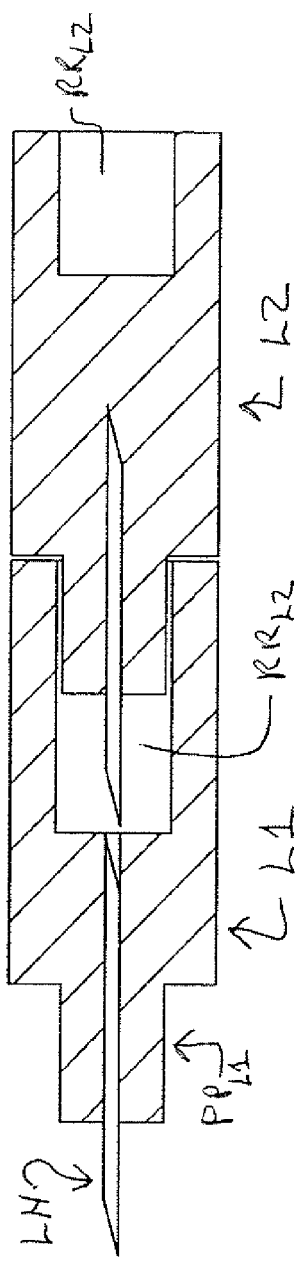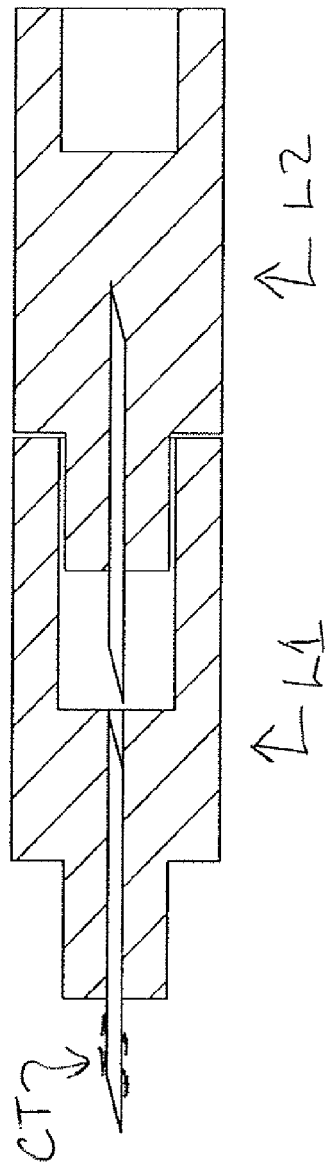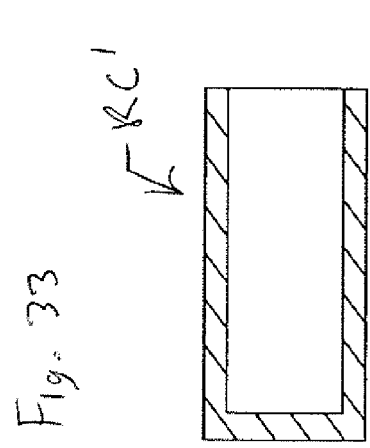

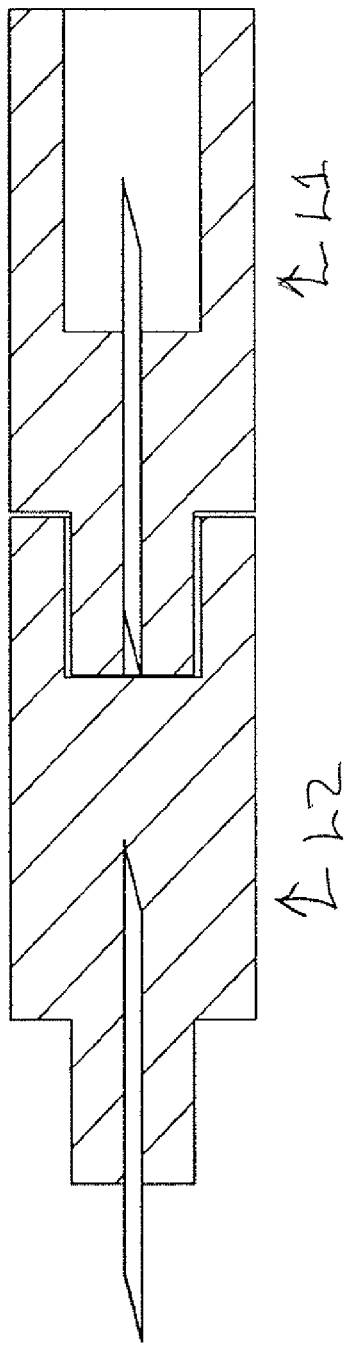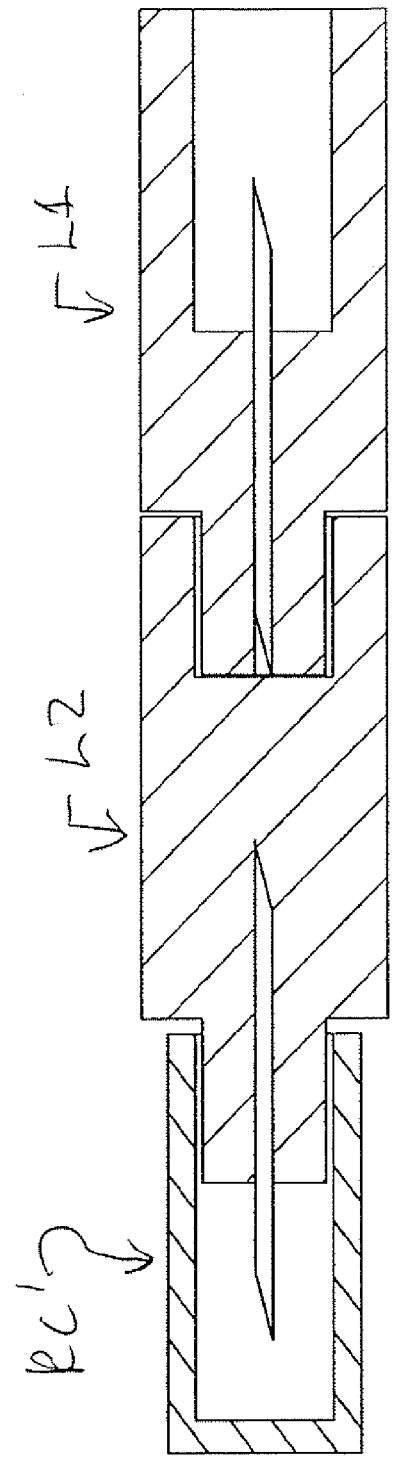
Fig. 40
Fig. 41

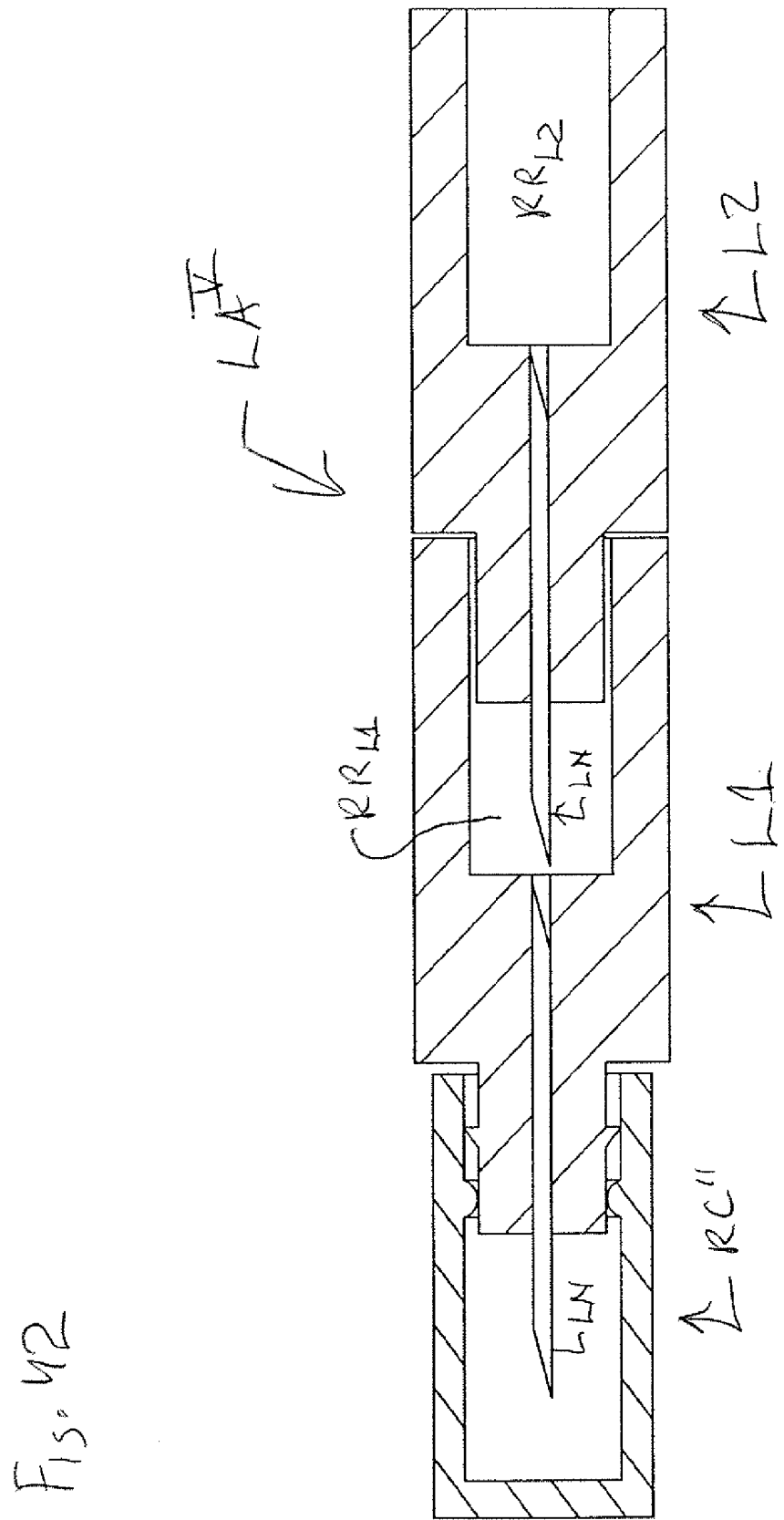

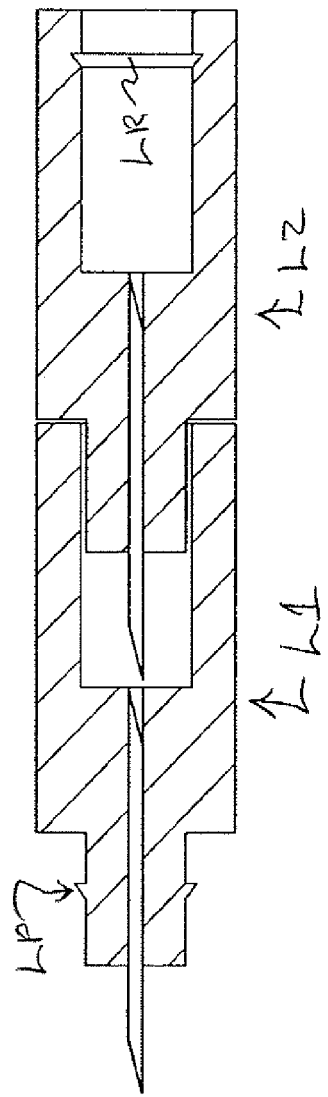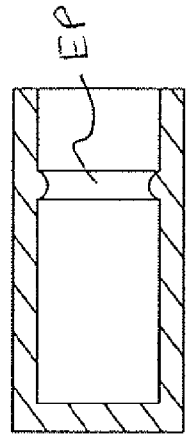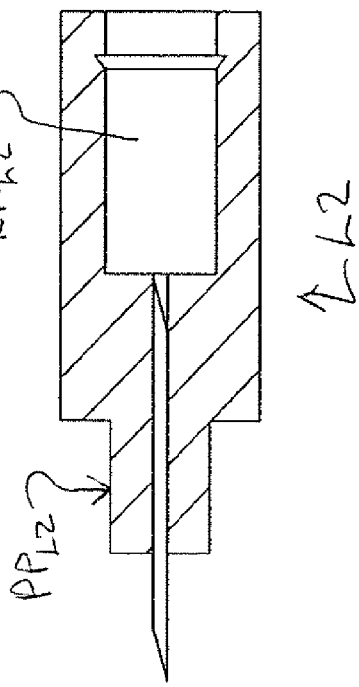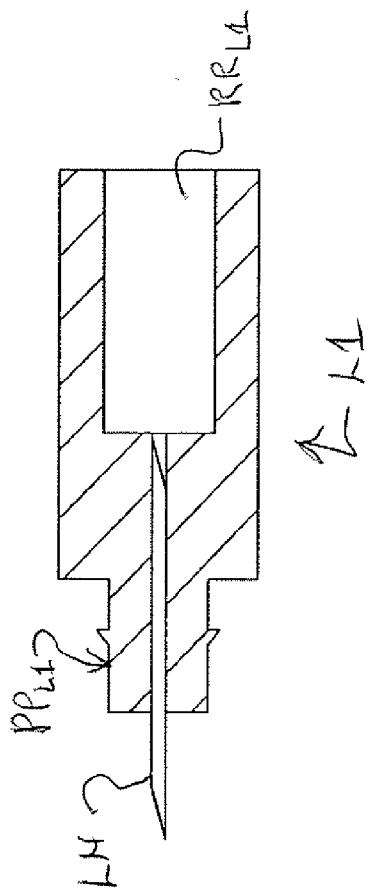

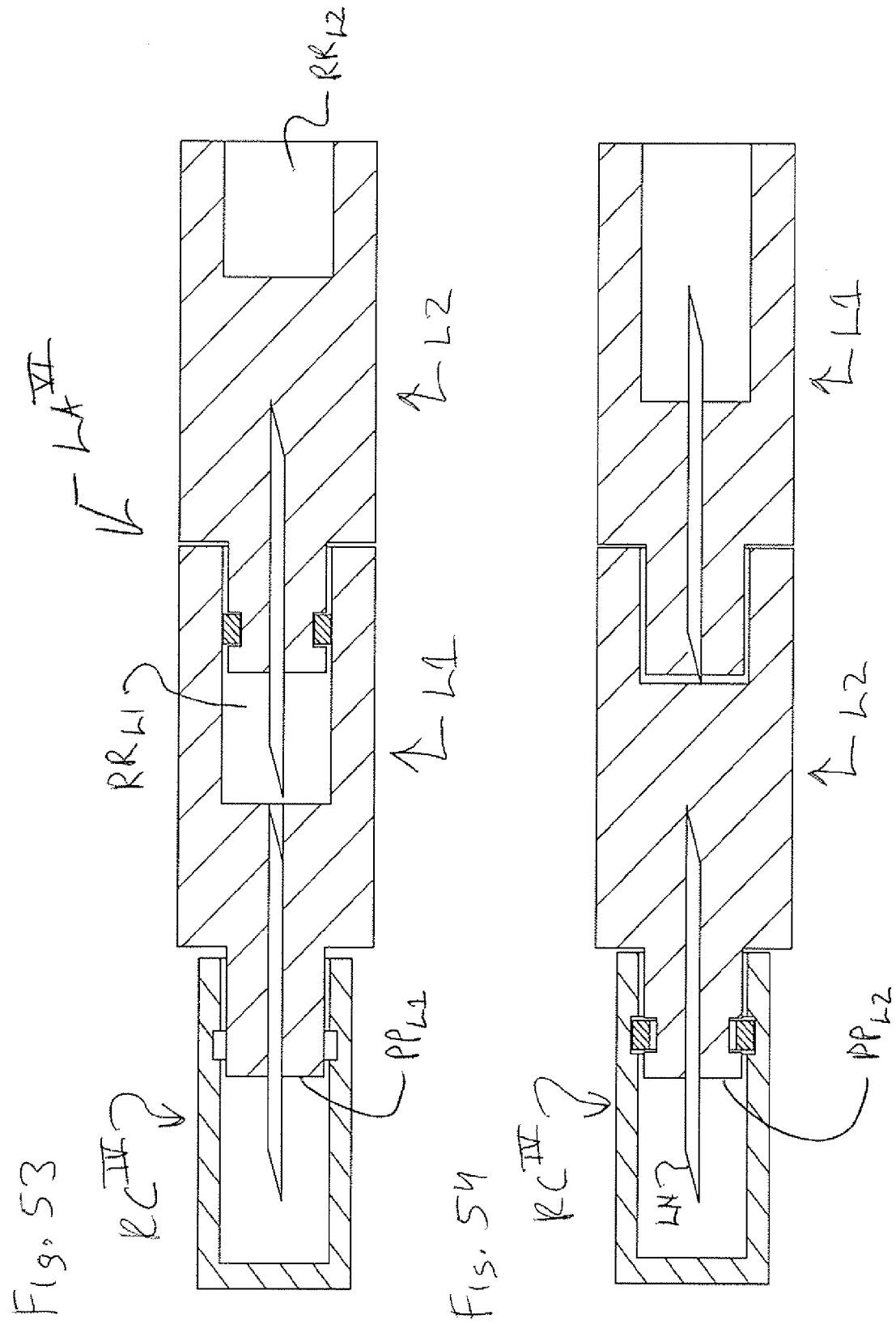

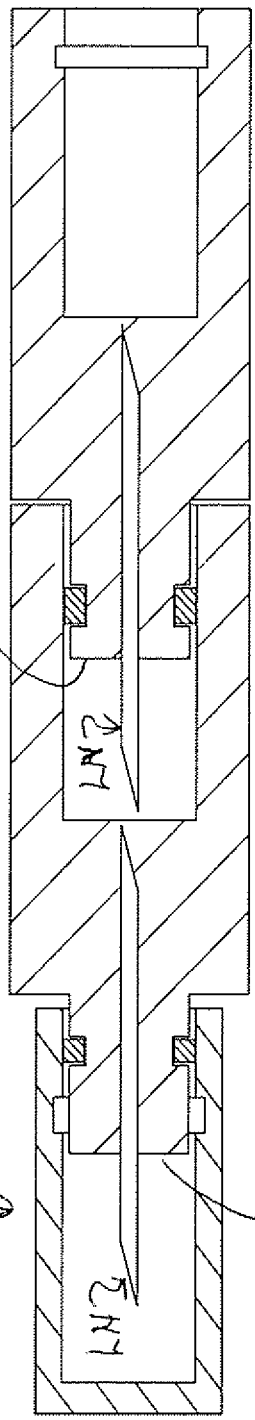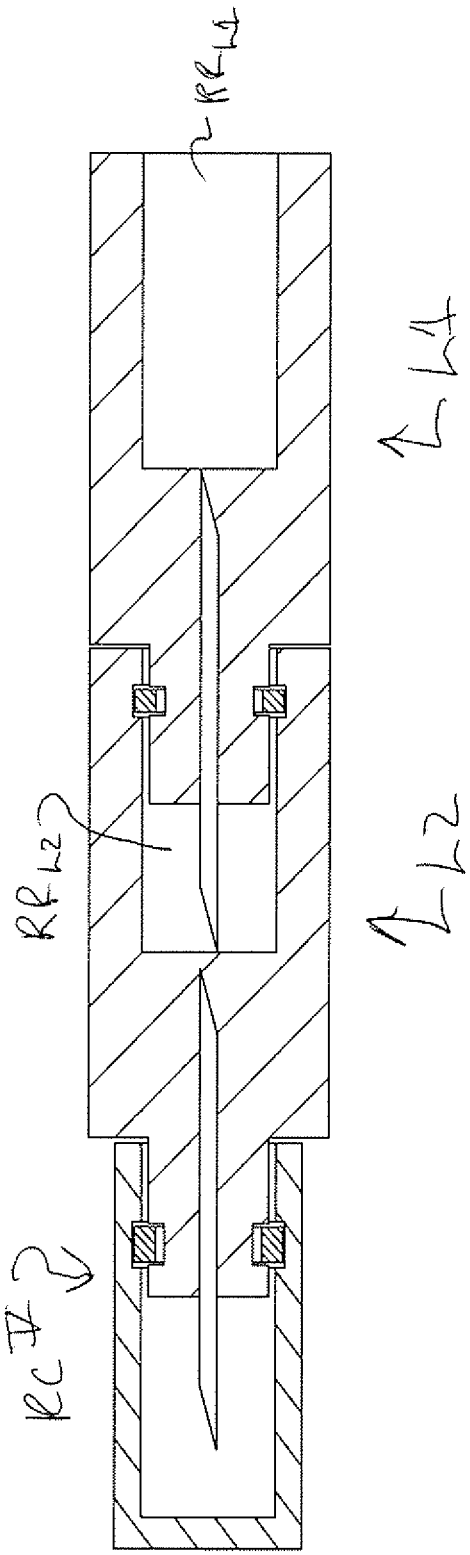

MULTI-LANCET UNIT, METHOD AND LANCET DEVICE USING THE MULTI-LANCET UNIT, AND METHOD OF ASSEMBLING AND/OR MAKING THE MULTI-LANCET UNIT

CROSS-REFERENCE TO RELATED APPLICATIONS

The present application is a continuation-in-part of U.S. application Ser. No. 11/044,008 filed Jan. 28, 2005, the disclosure of which is expressly incorporated by reference herein in its entirety.

BACKGROUND OF THE INVENTION

1. Field of the Invention

The invention relates to a multi-unit lancet in which a plurality of lancets are arranged in series and/or one in front of the other. The lancets are removably connected to each other and can be disconnected from each other by twisting, pulling, bending, and/or any combination of these movements. The invention also relates to a method of assembling and/or forming the multi-unit lancet assembly by individually forming each lancet, arranging them in a row and connecting the lancets together in order to form a multi-lancet unit. The invention further relates to a lancet device which uses the multi-lancet unit and to a method of using the lancet device to puncture a user's skin.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

SUMMARY OF THE INVENTION

According to one illustrative aspect of the invention there is provided a multi-lancet unit for a lancet device, wherein the unit preferably comprises a plurality of lancets arranged in a row. Each lancet preferably comprises a front end, a needle which extends from the front end, and a rear end. Preferably, the front end of at least one of the plurality lancets is removably connected to the rear end of another of the plurality of lancets.

The plurality of lancets may comprise at least two lancets. The plurality of lancets may comprise at least three lancets. The plurality of lancets may be between five lancets and twenty lancets. The plurality of lancets may be between eight lancets and twelve lancets. Each of the plurality of lancets may comprise a generally cylindrical portion. Each of the plurality of lancets may comprise a non-circular cross-section when viewed perpendicular to a center axis of the plurality of lancets. Each of the plurality of lancets may comprise a locking mechanism. The locking mechanisms may be generally equally spaced. Each of the plurality of lancets may comprise a locking recess.

The invention also provides a lancet device utilizing the multi-lancet unit described above, wherein the lancet device comprises a body and a holding member which houses the multi-lancet unit.

The invention also provides a lancet device utilizing the multi-lancet unit described above, wherein the lancet device comprises a body, a trigger, and a movable holding member which houses the multi-lancet unit.

The invention also provides a lancet device utilizing the multi-lancet unit described above, wherein the lancet device comprises a body, a trigger, a movable holding member which houses the multi-lancet unit, and a mechanism for moving the holding member to a retracted trigger-set position.

The invention also provides a lancet device utilizing the multi-lancet unit described above, wherein the lancet device comprises a body, a holding member which houses the multi-lancet unit, and a mechanism for moving the multi-lancet unit within the holding member.

The invention also provides a method of puncturing a surface of skin using the lancet device described above, wherein the method comprises placing or arranging the lancet device adjacent against a user's skin and triggering the lancet device so that one of the plurality of lancet is caused to penetrate the user's skin.

The invention also provides a multi-lancet unit for a lancet device, wherein the unit comprises a plurality of lancets arranged in a row. Preferably, each lancet comprises a front end, a needle which extends from the front end, a rear end, an opening extending into the rear end, and a locking mechanism. Preferably, the front end of at least one of the plurality lancets is removably connected to the rear end of another of the plurality of lancets.

The plurality of lancets may comprise at least two lancets. The plurality of lancets may comprise at least three lancets. The plurality of lancets may be between five lancets and twenty lancets. The plurality of lancets may be between eight lancets and twelve lancets. Each of the plurality of lancets may comprise a generally cylindrical portion. Each of the plurality of lancets may comprise a non-circular cross-section when viewed perpendicular to a center axis of the plurality of lancets. The locking mechanism may comprise a tapered recess. The locking mechanisms may be generally equally spaced. The locking mechanism may comprise a locking recess.

The invention also provides a lancet device utilizing the multi-lancet unit described above, wherein the lancet device comprises a body and a holding member which houses the multi-lancet unit.

The invention also provides a lancet device utilizing the multi-lancet unit described above, wherein the lancet device comprises a body, a trigger, and a movable holding member which houses the multi-lancet unit.

The invention also provides a lancet device utilizing the multi-lancet unit described above, wherein the lancet device comprises a body, a trigger, a movable holding member which houses the multi-lancet unit; and a mechanism for moving the holding member to a retracted trigger-set position.

The invention also provides a lancet device utilizing the multi-lancet unit described above, wherein the lancet device comprises a body, a holding member which houses the multi-lancet unit, and a mechanism for moving the multi-lancet unit within the holding member.

The invention also provides a method of puncturing a surface of skin using the lancet device described above, wherein the method comprises arranging the lancet device adjacent against a user's skin and triggering the lancet device so that one of the plurality of lancet is caused to penetrate the user's skin.

The invention also provides a method of making the multi-lancet unit described above, wherein the method comprises forming each of the plurality of lancets and arranging the plurality of lancets in a row to form the multi-lancet unit.

The invention also provides a multi-lancet unit for a lancet device, wherein the unit comprises a plurality of lancets arranged in a row. Each lancet comprises a front end, a needle which extends from the front end, a rear end, an opening extending into the rear end, and a locking mechanism. A plurality of breakable and/or separable connections is utilized. Each breakable or separable connection is arranged to connect an adjacent pair of lancets.

The invention also provides a multi-lancet unit for a lancet device, wherein the unit comprises a plurality of lancets arranged one in front of the other and each lancet comprising a front end, a needle which extends from the front end, and a rear end. The front end of at least one of the plurality lancets is removably connected to the rear end of another of the plurality of lancets.

The plurality of lancets may comprise two lancets. The plurality of lancets may comprise at least three lancets. The plurality of lancets may be between five lancets and twenty lancets. The plurality of lancets may be between eight lancets and twelve lancets. Each of the plurality of lancets may comprise a generally cylindrical portion. Each of the plurality of lancets may comprise a non-circular cross-section when viewed perpendicular to a center axis of the plurality of lancets. At least one of the plurality of lancets may comprise a locking mechanism. The locking mechanism may be one of a locking recess and a locking projection. At least one of the plurality of lancets may comprise at least one of a locking recess and a locking member. The needle of at least one of the plurality of lancets may be retractable.

The invention also provides a lancet device utilizing the multi-lancet unit described above, wherein the lancet device comprises a body and a holding member which houses the multi-lancet unit. The lancet device may also comprise a body, a trigger, a movable holding member which is configured to receive the multi-lancet unit, and a mechanism for moving the holding member to a retracted trigger-set position. The lancet device may comprise a body, a holding member which receives the multi-lancet unit, and a mechanism for moving the multi-lancet unit within the holding member.

The invention also provides a method of puncturing a surface of skin using the lancet device described above, wherein the method comprises arranging the lancet device adjacent against a user's skin and triggering the lancet device so that one of the plurality of lancet is caused to penetrate the user's skin. The invention also provides a method of puncturing a surface of skin using the lancet device described above, wherein the method comprises arranging the lancet device adjacent against a user's skin and triggering the lancet device so that one of the plurality of lancet is caused to penetrate the user's skin. The invention also provides a method of puncturing a surface of skin using the lancet device described above, wherein the method comprises arranging the lancet device adjacent against a user's skin and triggering the lancet device so that one of the plurality of lancet is caused to penetrate the user's skin.

The invention also provides a multi-lancet unit for a lancet device, wherein the unit comprises a plurality of lancets arranged in a row and each lancet comprising a front end, a needle which extends from the front end, a rear end, an opening extending into the rear end. The front end of at least one of the plurality lancets is removably connected to the rear end of another of the plurality of lancets.

The plurality of lancets may comprise two lancets. Each of the plurality of lancets comprises a generally cylindrical portion. Each of the plurality of lancets may comprise a non-circular cross-section when viewed perpendicular to a center axis of the plurality of lancets. One of the plurality of lancets may be configured to be non-removably connected to another of the plurality of lancets. One of the plurality of lancets may be configured to be non-removably connected to another of the plurality of lancets after said lancets are separated from each other and connected to each other in a different configuration. The unit may further comprise a cap which is configured to be removably connected to one of the plurality of lancets and configured to be non-removably connected to another of the plurality of lancets.

The invention also provides a lancet device utilizing the multi-lancet unit described above, wherein the lancet device comprises a body and a holding member which houses the multi-lancet unit.

The invention also provides a lancet device utilizing the multi-lancet unit described above, wherein the lancet device comprises a body, a trigger, and a movable holding member which receives or supports the multi-lancet unit.

The invention also provides a lancet device utilizing the multi-lancet unit described above, wherein the lancet device comprises a body, a movable holding member which receives or supports the multi-lancet unit, a mechanism for moving the holding member to a retracted trigger-set position, and at least one of: a front cap arrangement connected to the body; a front tip assembly coupled to a front end of the body; a front assembly removably coupled to a front end of the body; and a tip assembly adjusting a penetration depth of a lancet needle being coupled to a front end of the body.

The invention also provides a lancet device utilizing the multi-lancet unit described above, wherein the lancet device comprises a body, a holding member which houses the multi-lancet unit, and a mechanism for moving the multi-lancet unit within the holding member.

The invention also provides a method of puncturing a surface of skin using the lancet device described above, the method comprises arranging the lancet device adjacent against a user's skin and triggering the lancet device so that one of the plurality of lancet is caused to penetrate the user's skin.

The invention also provides a method of puncturing a surface of skin using the lancet device described above, wherein the method comprises arranging the lancet device adjacent against a user's skin and triggering the lancet device so that one of the plurality of lancet is caused to penetrate the user's skin.

The invention also provides a method of puncturing a surface of skin using the lancet device described above, wherein the method comprises arranging the lancet device adjacent against a user's skin and triggering the lancet device so that one of the plurality of lancet is caused to penetrate the user's skin.

The invention also provides a method of making the multi-lancet unit described above, wherein the method comprises forming each of the plurality of lancets and arranging the plurality of lancets in a row to form the multi-lancet unit.

The invention also provides a method of making the multi-lancet unit described above, wherein the method comprises forming each of the plurality of lancets and arranging the plurality of lancets in a row to form the multi-lancet unit.

The invention also provides a multi-lancet unit for a lancet device, wherein the unit comprises a plurality of lancets arranged in a row, each lancet comprising a front end, a needle which extends from the front end, a rear end, an opening extending axially into the rear end, and a cap removably connected to a front one of the plurality of lancets.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 13 shows a view similar to that of FIG. 12 with the front most lancet being removed from the multi-lancet unit;

FIG. 33 shows a cross-section view of the cap which can be used on the multi-lancet unit of FIG. 32. The cap has the form of a generally cylindrical sleeve with an closed front end and an open rear end;

FIG. 34 shows a cross-section view of the multi-lancet unit shown in FIG. 32 with the cap removed;

FIG. 35 shows a cross-section view of the multi-lancet unit shown in FIG. 32 with the cap removed and after the multi-lancet unit is used to puncture the skin of a user. The needle which has been used is shown to have contaminates, e.g., blood;

FIG. 40 shows a cross-section view of the multi-lancet unit shown in FIG. 32 and after the multi-lancet unit is used to puncture the skin of a user and after the front lancet has been separated from the rear lancet and inserted into the rear lancet. At this point, the multi-lancet unit is ready to again puncture the skin of a user with a fresh needle, i.e., the needle of the rear lancet which has assumed the position of the front lancet. When the front lancet was positioned in the rear end of the rear lancet, the needle was forced to retract into the lancet;

FIG. 41 shows a cross-section view of the multi-lancet unit after it has been used a second time to puncture the skin of a user. The cap is now removably connected the rear lancet which has become the front lancet;

FIG. 42 shows a cross-section view of another embodiment of the multi-lancet unit. This embodiment utilizes two or more lancets which each have a front projecting portion and a rear recess portion. A cap is removably connected the from front projecting portion of the first lancet;

FIG. 43 shows a cross-section view of the cap which can be used on the multi-lancet unit of FIG. 42. The cap has the form of a generally cylindrical sleeve with an closed front end and an open rear end;

FIG. 44 shows a cross-section view of the multi-lancet unit shown in FIG. 42 with the cap removed;

FIG. 45 shows a cross-section view of the front lancet of the multi-lancet unit shown in FIG. 42 and after the multi-lancet unit is used to puncture the skin of a user and after the front lancet has been separated from the rear lancet;

FIG. 46 shows a cross-section view of the rear lancet of the multi-lancet unit shown in FIG. 42 and after the multi-lancet unit is used to puncture the skin of a user and after the front lancet has been separated from the rear lancet;

FIG. 53 shows a cross-section view of still another embodiment of the multi-lancet unit. This embodiment utilizes two or more lancets which each have a front projecting portion and a rear recess portion. A cap is removably connected the from front projecting portion of the first lancet;

FIG. 54 shows a cross-section view of the multi-lancet unit of FIG. 53 after it has been used a second time to puncture the skin of a user. The cap is now non-removably connected to the rear lancet which has become the front lancet;

FIG. 55 shows a cross-section view of still another embodiment of the multi-lancet unit. This embodiment utilizes two or more lancets which each have a front projecting portion and a rear recess portion. A cap is removably connected the from front projecting portion of the first lancet; and FIG. 56 shows a cross-section view of the multi-lancet unit of FIG. 55 after it has been used a second time to puncture the skin of a user. The cap is now non-removably connected to the rear lancet which has become the front lancet. The front lancet has also become non-removably connected to the rear end of the rear lancet, which is now the front lancet.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
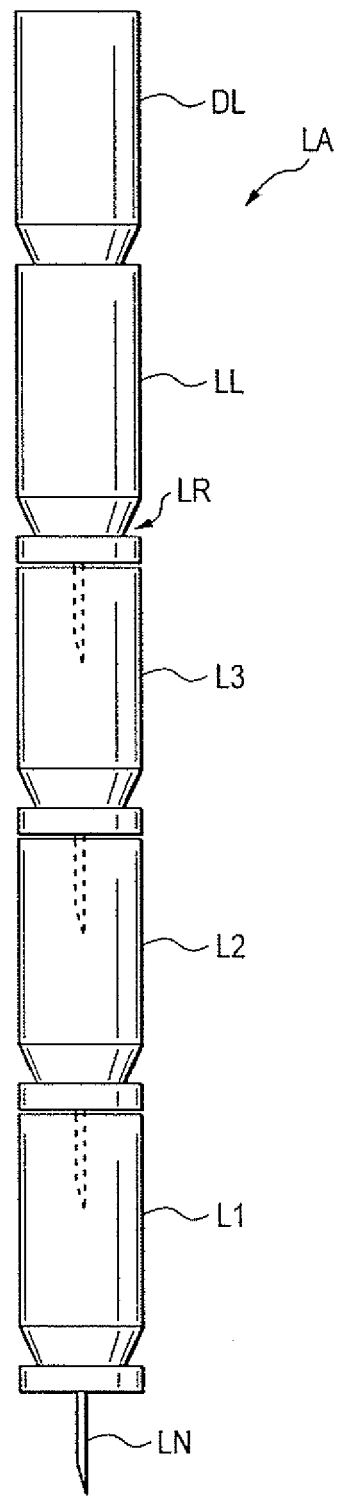
FIG. 1 shows a side view of one embodiment of a multi-lancet unit. The unit includes four removably connected lancets arranged one in front of the other. Each lancet includes a lancet needle.
Figure 2:
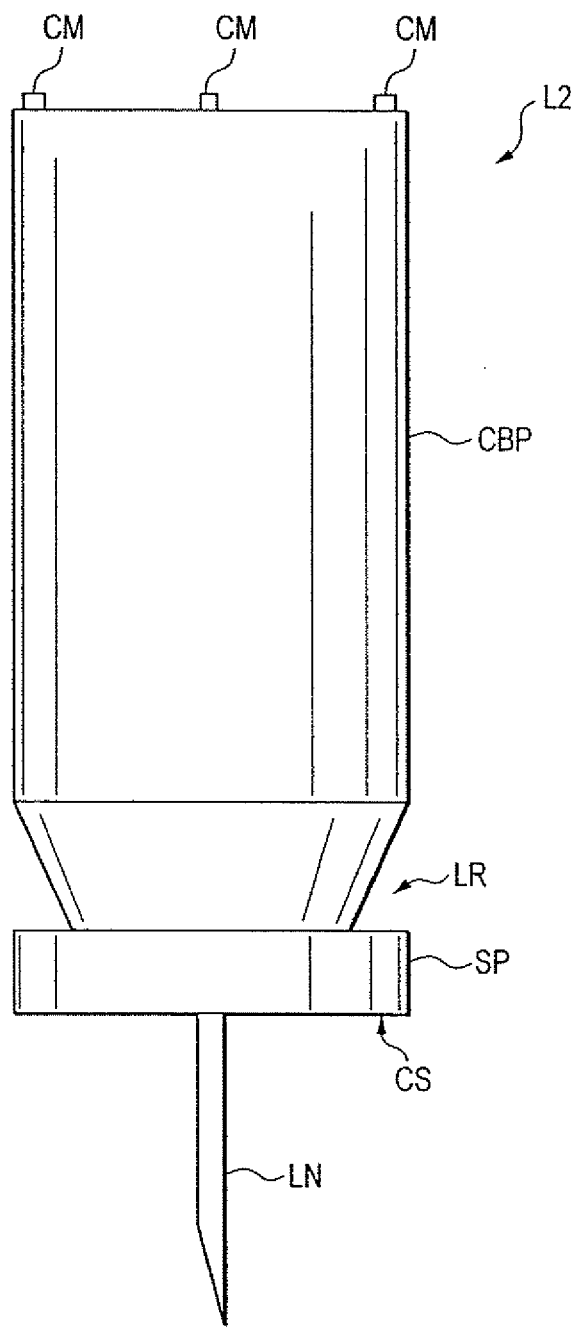
FIG. 2 shows an enlarged view of the second lancet shown in the unit of FIG. 1.
Figure 3:
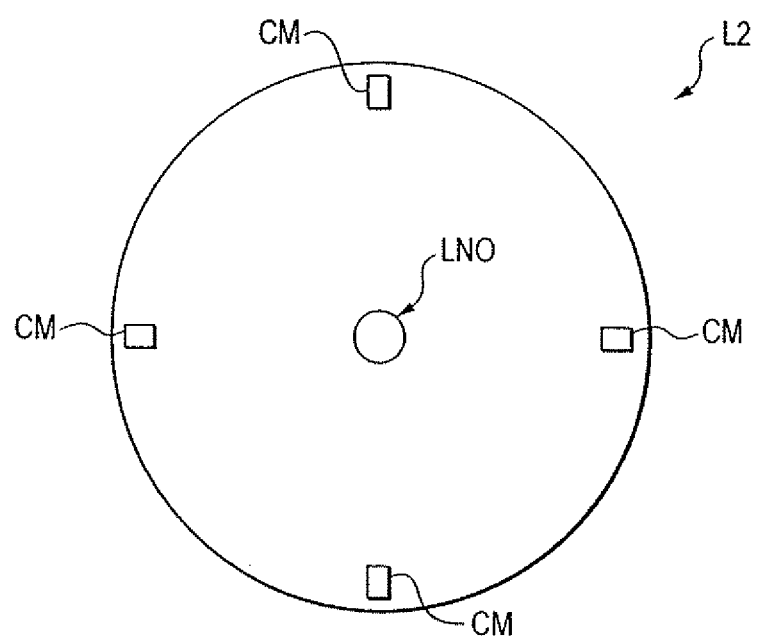
FIG. 3 shows a top view of the lancet shown in FIG. 2.
Figure 4:
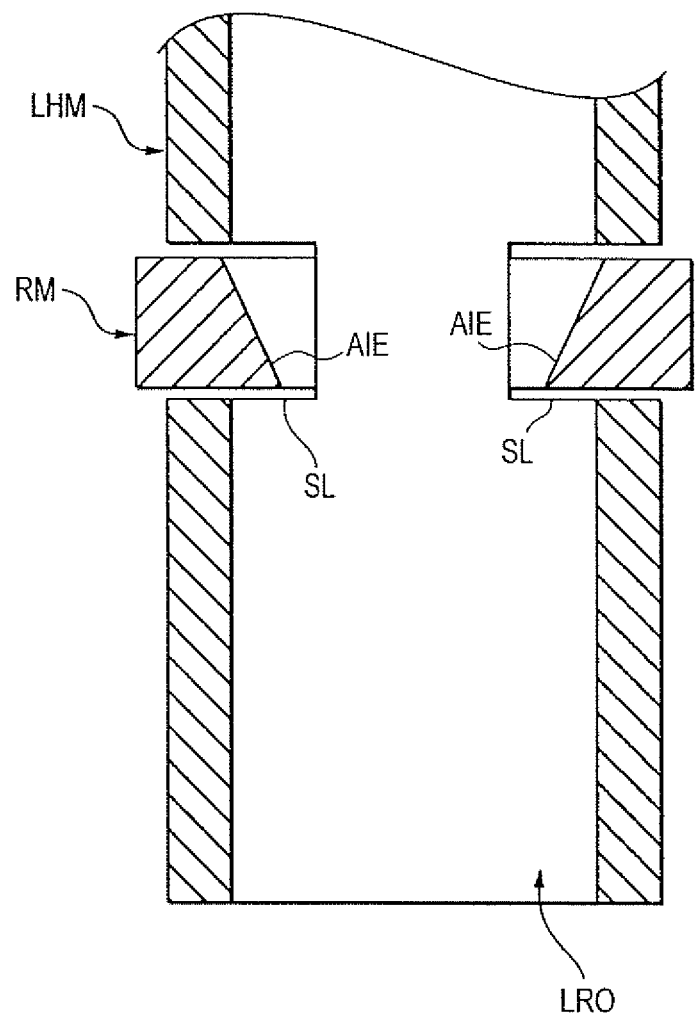
FIG. 4 shows a cross-section view of an end portion one embodiment of a lancet holding member.
Figure 5:
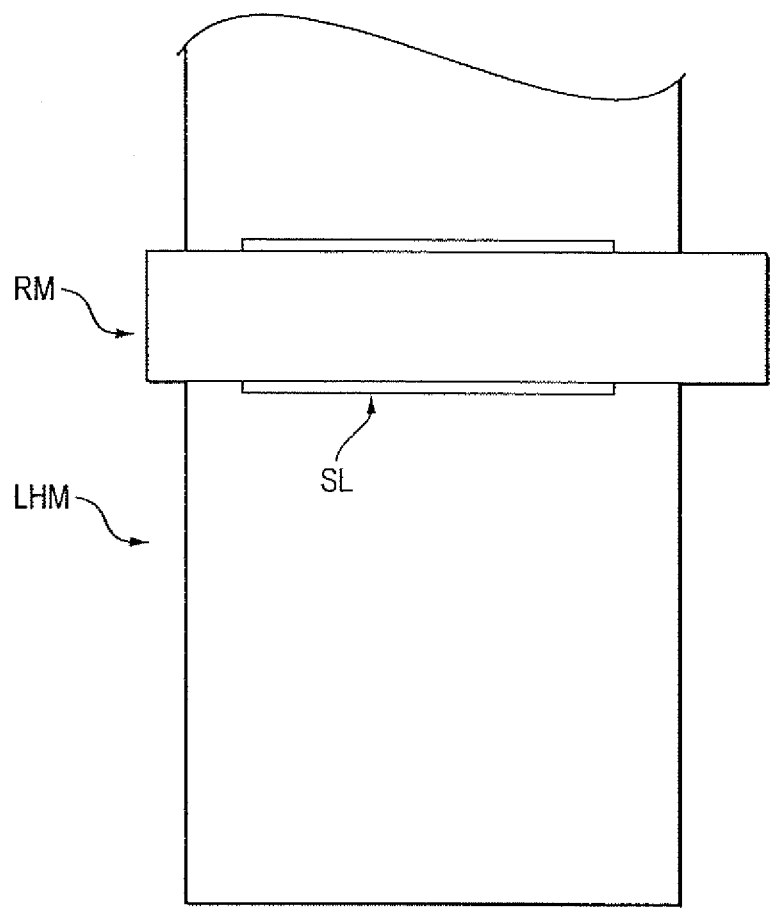
FIG. 5 shows a side view of FIG. 4.
Figure 6:
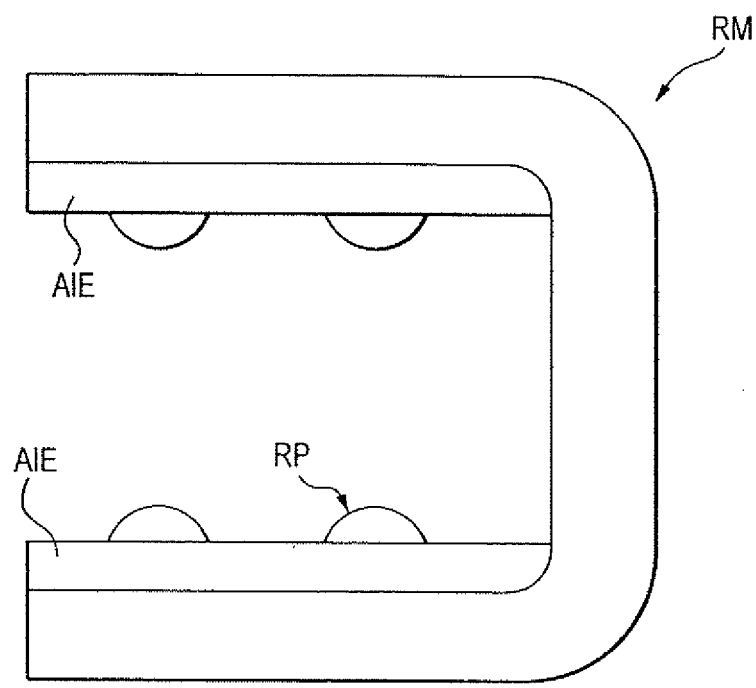
FIG. 6 shows a top view of the retaining member used on the embodiment shown in FIGS. 4 and 5.
Figure 7:
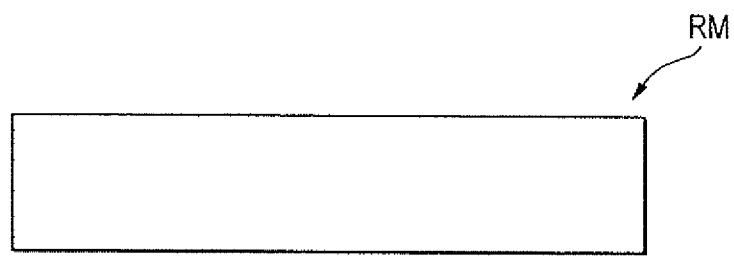
FIG. 7 shows a side view of the retaining member shown in FIG. 6.
Figure 8:
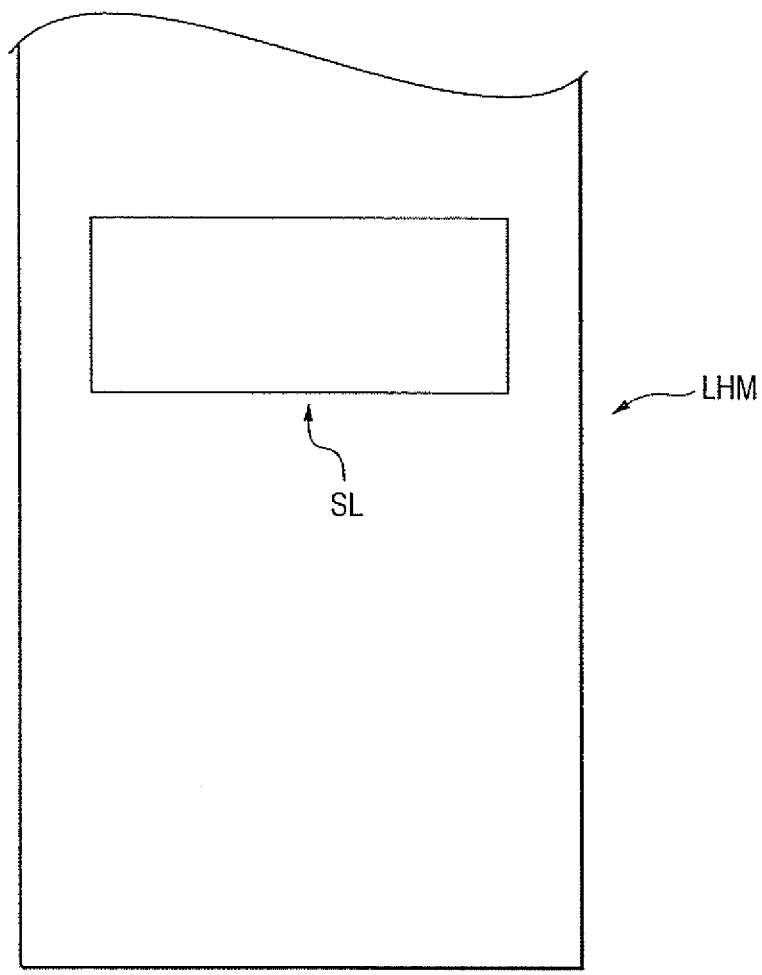
FIG. 8 shows a side view of the lancet holding member shown in FIG. 5 with the retaining member removed.
Figure 9:
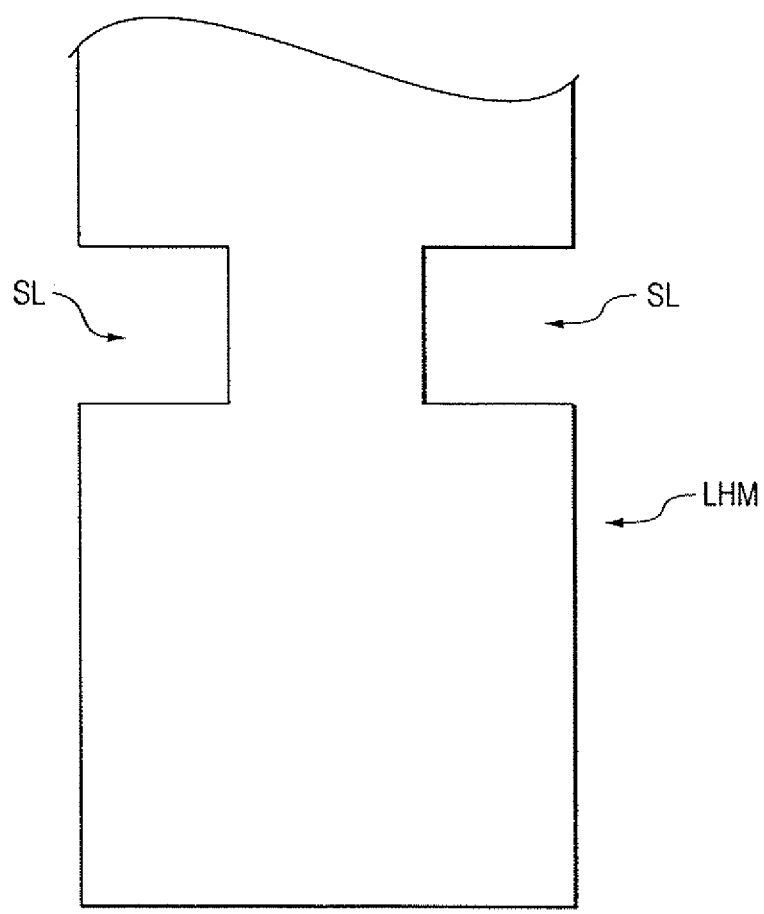
FIG. 9 shows another side view of the lancet holding member shown in FIG. 5. The view is rotated 90 degrees from that shown in FIG. 8.
Figure 10:
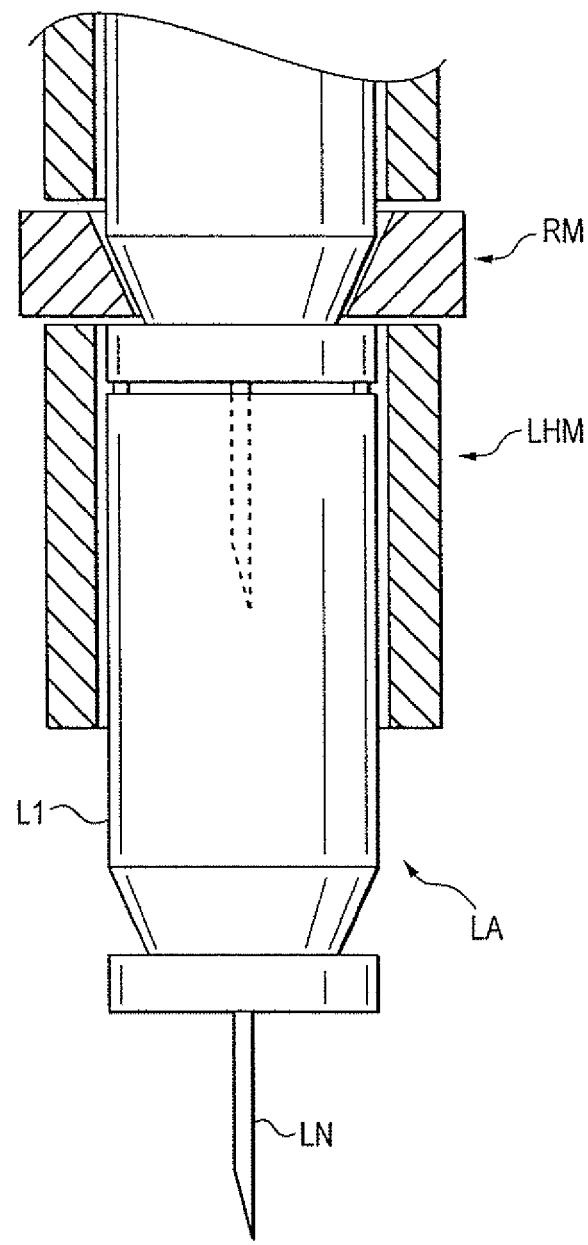
FIG. 10 shows a cross-section view of the lancet holding member shown in FIGS. 4, 5, 8 and 9 with the multi-lancet unit installed therein. The lancets are not shown in cross-section.
Figure 11:
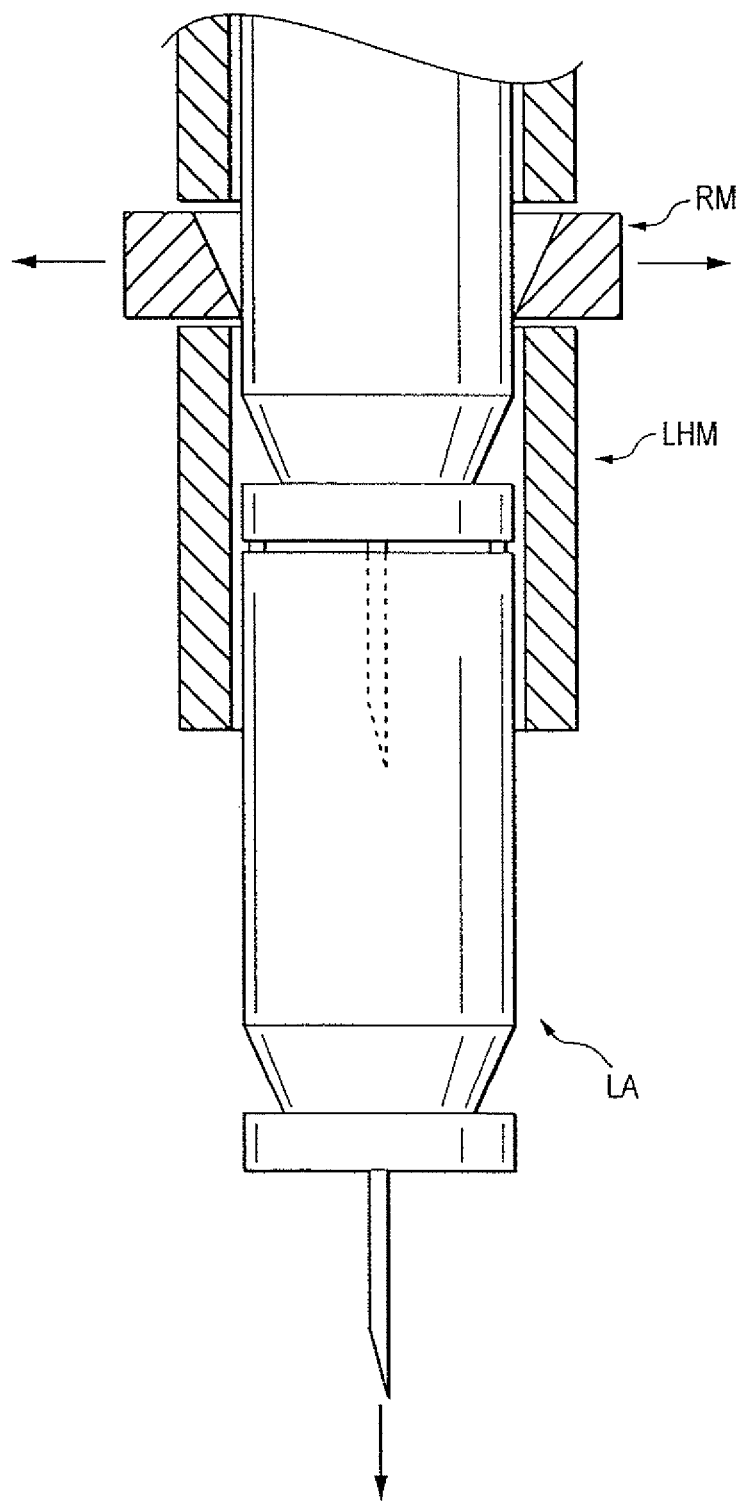
FIG. 11 shows a view similar to that of FIG. 10 with the multi-lancet unit being moved and/or advanced partially forward and out of the lancet holding member.
Figure 12:
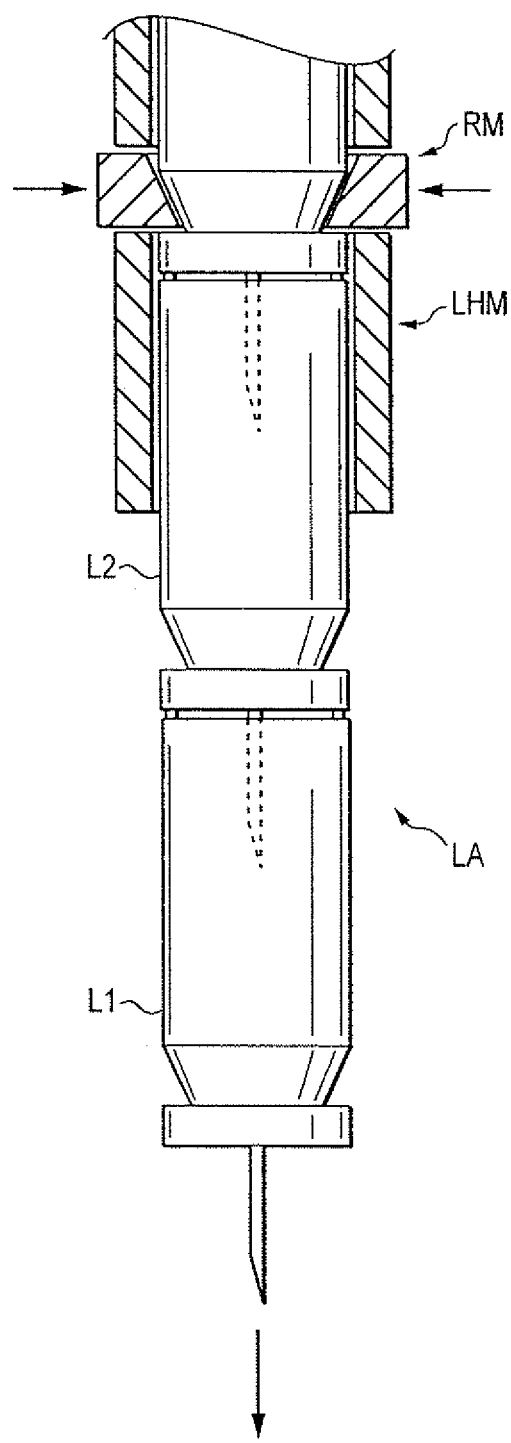
FIG. 12 shows a view similar to that of FIG. 11 with the multi-lancet unit being moved and/or advanced forward and out of the lancet holding member until the retaining member engages the next lancet thereby temporarily locking the multi-lancet unit in the next position.

FIGS. 1-3 show a first non-limiting embodiment of a lancet assembly or multi-lancet unit LA. The unit LA includes a plurality of lancets L1, L2, L3 and a terminating or rear end lancet which is made up of a last lancet LL and a dummy lancet DL. These rear lancet members LL and DL are preferably non-removably connected to each other. The last lancet LL and the lancets L1-L3 (or L1-LN depending on the desired number N of lancets in a unit LA) are generally identical in size, shape and configuration with the exception that the last lancet LL need not be provided with the connecting members CM. Instead, the last lancet LL and the dummy lancet DL can be formed as a one-piece member. As can be seen in FIG. 2, each lancet, e.g., lancet L1, has body portion CBP which can be generally cylindrical. As can be seen in FIG. 3, a rear end of each lancet, e.g., lancet L1, includes a plurality of connecting projections or members CM and a generally centrally arranged lancet needle opening LNO which is sized to receive therein a lancet needle LN of an adjacent rear lancet, e.g., lancet L2. The particular number, size, shape and arrangement of the connecting members CM is not of particular importance provided that a stable yet breakable connection is ensured between the adjacent lancets. In this regard, the connection should be strong enough to allow a user pull the unit LA out of the lancet holding member LHM (see FIGS. 11 and 12) until the unit LA reaches the next locking or retaining position to allow for the use of a new lancet, e.g., the next adjacent lancet L2. The connection should also be weak enough to allow the user to break off (see FIG. 13) the front lancet, e.g., to allow the user to break off the lancet L1 from the rear adjacent lancet L2. In this regard, the invention contemplates that the connection can be formed by any convenient and/or practical arrangement such as, e.g., adhesively bonding or ultrasonically welding, the members CM to the contact surfaces CS. The connection can also be made breakable in any desired way provided that a user can cause separation of the lancets in a simple way by, e.g., twisting and/or bending. As can be seen in FIG. 13, breaking off the front lancet L1 exposes the lancet needle LN of the rear adjacent lancet L2. As a result, the lancet needle LN of the rear adjacent lancet L2 remains protected within the opening LNO of the front lancet L1 while the front lancet L1 is connected to the rear adjacent lancet L2.

Each lancet, e.g, lancet L1, also includes a front end from which the lancet needle LN extends or projects. A locking or retaining recess LR and a shoulder SP whose front surface forms a contact surface CS is also provided on each lancet. By way of non-limiting example, the locking recess LR can be a tapered recess and can be specifically designed to engage with a locking or retaining member RM of a lancet holding member LHM of a lancet device (see FIGS. 4-13). Of course, other mechanisms, other than a locking recess, can be utilized to ensure that the lancet unit LA is indexed or advanced in generally equal increments within the lancet holding member LHM. The invention contemplates that the particular location, size and configuration of the retaining mechanism of each lancet can be specifically configured to a particular lancet holding member LHM of a particular lancet device.

Figure 30:
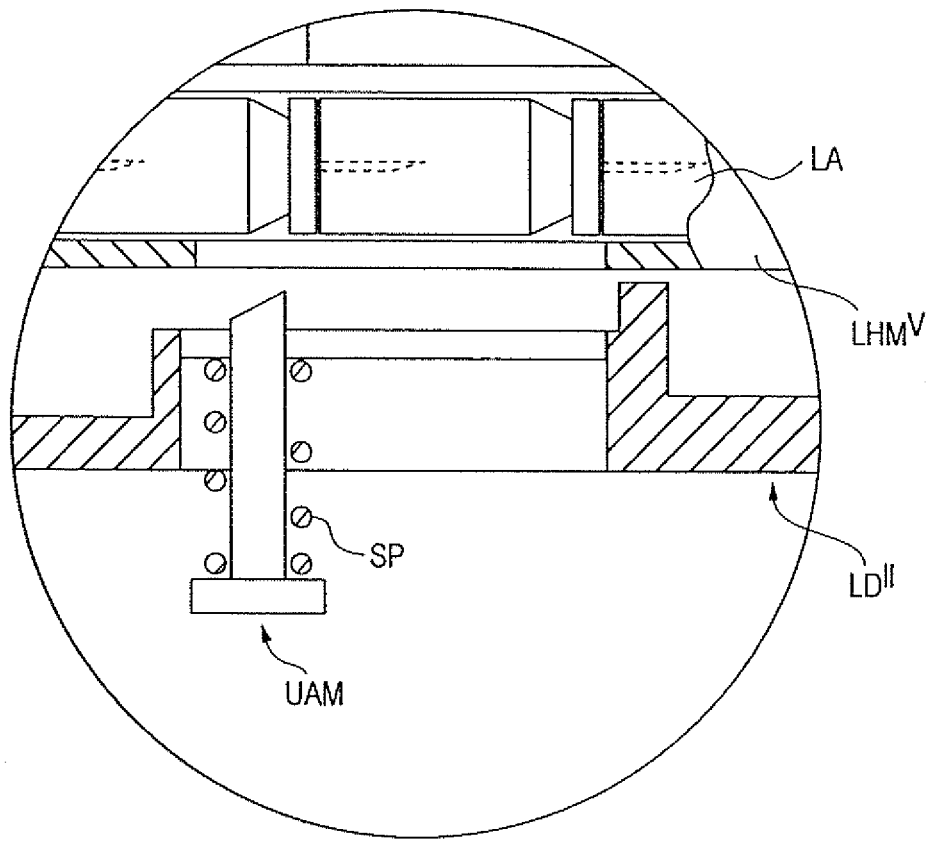
FIG. 30 shows an enlarged view of the multi-lancet unit advancing system shown in FIG. 29.
Figure 31:
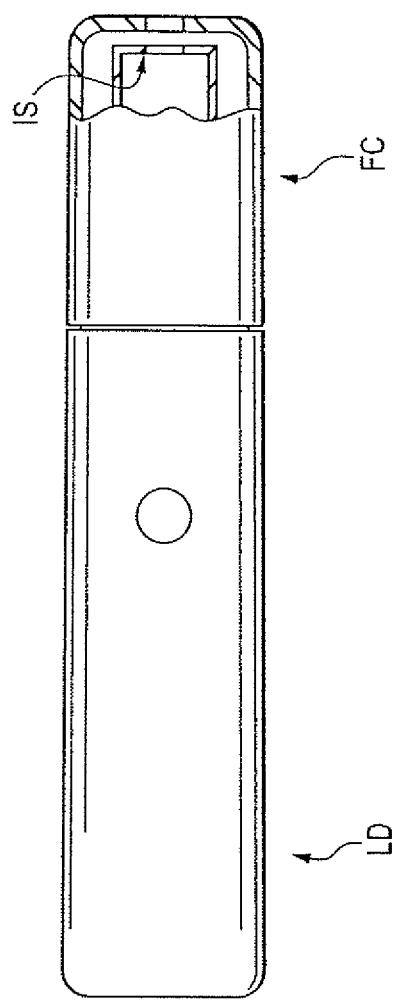
FIG. 31 schematically shows a lancet device with a front cap.

The contact surface CS can be designed to contact an inner surface IS (which can be a movable/adjustable surface) of a lancet device tip (see e.g., FIG. 31). By way of non-limiting examples, the unit LA can be used with a lancet device (i.e., any of the lancet devices disclosed herein) which includes an adjustable tip or front cap FC (see FIG. 31) of the type described in any one of the following documents: U.S. Pat. No. 6,811,557 to SCHRAGA, U.S. Pat. No. 6,530,937 to SCHRAGA, U.S. Pat. No. 6,322,575 to SCHRAGA, and U.S. Pat. No. 5,613,978 to HARDING, the disclosures of which are hereby expressly incorporated by reference in their entireties. By way of non-limiting examples, the unit LA can also be used with a lancet device (i.e., any of the lancet devices disclosed herein) which includes a non-adjustable tip or front cap FC (see FIG. 31) of the type described in any one of the following documents: U.S. Pat. No. 6,156,051 to SCHRAGA, U.S. Pat. No. 6,022,366 to SCHRAGA, U.S. Pat. No. 5,908,434 to SCHRAGA, U.S. Pat. No. 5,797,942 to SCHRAGA, U.S. Pat. No. 5,628,764 to SCHRAGA, and U.S. Pat. No. 5,464,418 to SCHRAGA, the disclosures of which are hereby expressly incorporated by reference in their entireties. The above noted tips, as well as any of the tips known in the prior art, can also be used with any of the lancet devices described herein such as the ones shown in FIGS. 17, 18, 20-23, 26 and 28-30. Additionally, the tip or front cap FC can be secured (e.g., non-removably secured or removably secured) to the lancet devices disclosed herein by any conventionally known arrangements such as threads, a snap connection, etc.

The body CBP of the lancets L1, L2, L3, LL and DL can be made of any conventional material of which conventional lancets are made such as, e.g., synthetic resin. They can also be made by any conventional lancet making techniques including, e.g., injection molding, extrusion, etc. The lancet needles LN can also be of the same material, types and sizes as are used in conventional lancets. The number of lancets in a particular unit LA can also vary depending on the desired number required for a unit LA. It will also depend on the desired overall axial length of the unit LA. Preferably, the overall unit LA has an axial length of between approximately 1" and approximately 5" depending on the number of lancets in a unit LA and the length of each lancet. By way of non-limiting example, each lancet can also range in axial length between approximately ¼" and approximately ¾". In order to provide a visual indicator to a user, the last lancet LL, and optionally also lancet DL, can be made of different color than the lancets L1-L3. In this way, when the user uses the unit LA in a lancet device (see e.g., FIGS. 17-19), upon seeing and using the last lancet LL, the user will be able to note that it is time to change the unit LA with a new unit LA.

FIGS. 4-13 illustrate one non-limiting way in which the unit LA can be mounted to a lancet holding member LHM of a lancet device. Generally speaking, most lancet devices utilize a lancet holding member. The lancet holding member is typically movably mounted within the lancet device and is usually moved and/or biased by one or more springs. In many lancet devices, the lancet holding member retains a replaceable lancet at a front location. Examples of such devices are disclosed in the following documents: U.S. Pat. No. 6,811,557 to SCHRAGA, U.S. Pat. No. 6,530,937 to SCHRAGA, U.S. Pat. No. 6,346,114 to SCHRAGA, U.S. Pat. No. 6,190,398 to SCHRAGA, U.S. Pat. No. 6,156,051 to SCHRAGA, U.S. Pat. No. 6,022,366 to SCHRAGA, U.S. Pat. No. 5,908,434 to SCHRAGA, U.S. Pat. No. 5,797,942 to SCHRAGA, U.S. Pat. No. 5,628,764 to SCHRAGA, U.S. Pat. No. 5,464,418 to SCHRAGA, and U.S. Pat. No. 5,613,978 to HARDING, the disclosures of which are hereby expressly incorporated by reference in their entireties. According to one non-limiting example, the lancet holding member of one or more of the devices disclosed in these documents is modified so as to use the unit LA disclosed herein. This can occur by redesigning the lancet holding member of these devices so as to be hollow or tubular to allow for axial insertion of the unit LA in a manner similar to that shown in the lancet device of, e.g., FIG. 20.

Again with reference to FIGS. 4-13, it can be seen that the lancet holding member LHM, which uses the unit LA, has a front end from which a lancet L1 extends and through which the unit LA moves through. In order to ensure that the unit LA advances and/or indexes out of the front end one lancet at a time, the lancet holding member LHM includes a retaining mechanism RM. In the embodiment shown in FIGS. 4-13, the retaining mechanism RM has the form of a C-shaped clip (see FIG. 6). The retaining mechanism RM mounted to front end of the lancet holding member LHM via oppositely arranged slots SL, which are sized slightly larger in width than the retaining member RM in order to loosely receive therein the retaining member RM. In order to ensure that the retaining member RM remains mounted to the lancet holding member LHM, the retaining member RM includes four retaining projections RP which are designed to prevent the retaining member RM from sliding out of engagement with the slots SL. The retaining member RM includes tapered and/or angled inner edges AIE which utilize an angle which is generally complementary to that of the retaining recesses LR (see FIG. 10). As can be seen when comparing FIGS. 10-12, the retaining member RM is made of a resilient or spring-like material which can be deflected outwards (see FIG. 11) when the unit LA is moved out of the front end of the lancet holding member LHM. The angles of the edge AIE and the recess LR are such that they facilitate outward deflection of legs of the retaining member RM when the unit LA is moved in the direction shown in FIG. 11. However, because the retaining member RM has the properties of a natural spring, when the unit LA is advanced out by the length of a lancet, the edges AIE again engage with another retaining recess LR thereby locking the unit LA in the next position (see FIG. 12).

Figure 29:
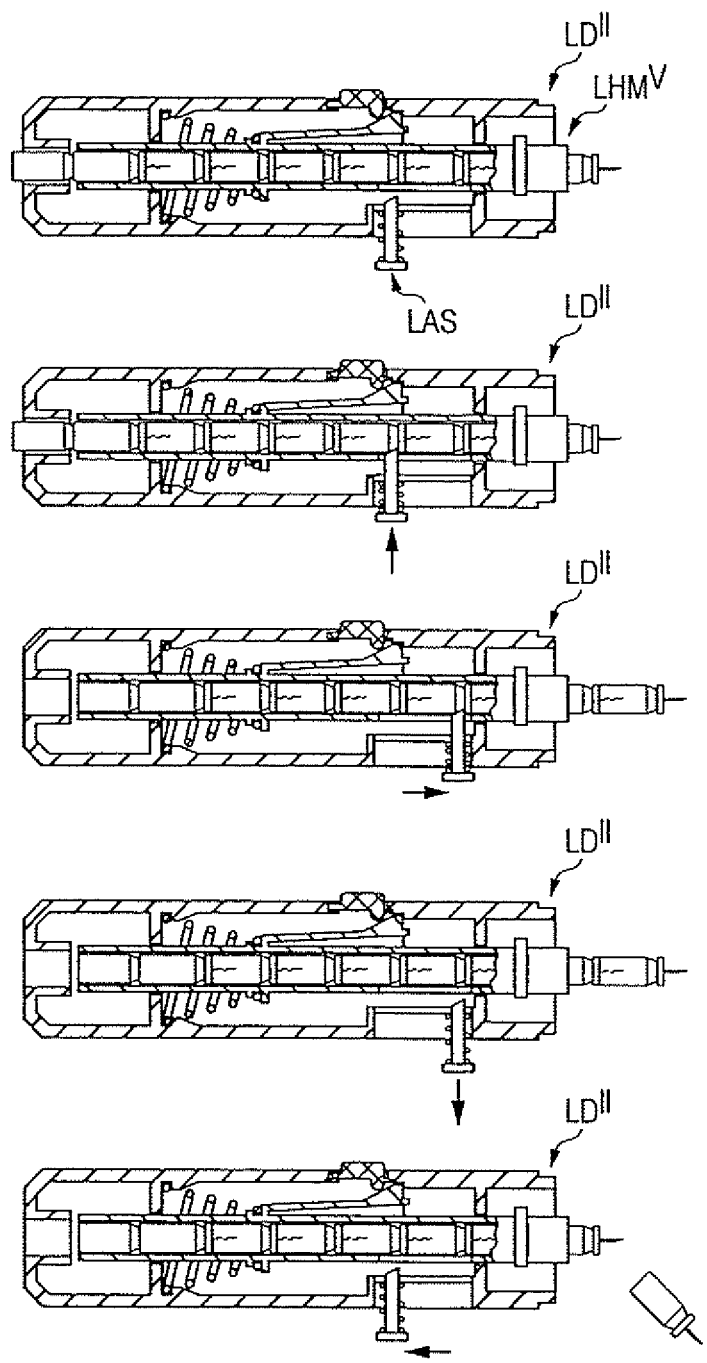
FIG. 29 shows five views of another embodiment of the lancet device wherein the lancet devices uses a system for advancing the multi-lancet unit. The mechanism has the form of a slide button. This multi-lancet unit advancing system can be used on any of the lancet devices disclosed herein.

According to this embodiment, the used lancet L1 can the be separated and/or broken off from the unit LA (see FIG. 13) using either a twisting motion and/or a bending motion. At this point, the lancet needle LN of the next or new lancet L2 is ready for use. The user can then install the tip of the lancet device and use it to pierce the skin. In this embodiment, the user grips the used lancet L1 and pulls on the used lancet L1 (FIG. 11) to cause the unit LA to advance forward. The retaining member RM, by virtue of its angled inner edge AIE, prevents the unit LA from moving back into the lancet holding member LHM even if the user desired it to so move, which functions as a safety feature. Of course, pulling of the lancet L1 has the possibility of pricking the user because the lancet needle LN is exposed. Accordingly, it is preferred that the lancet device, which uses the lancet holding member LHM shown in FIGS. 4-13, also use a system for advancing the unit LA that does not require the user to handle the lancets during pulling, even though it may be necessary to do so to disconnect the lancet L1 from the lancet L2. By way of non-limiting example, FIGS. 29 and 30 show one such a system which can be used with any of the lancet holding members described herein. The details of FIGS. 29 and 30 will be described later on.

Figure 14:
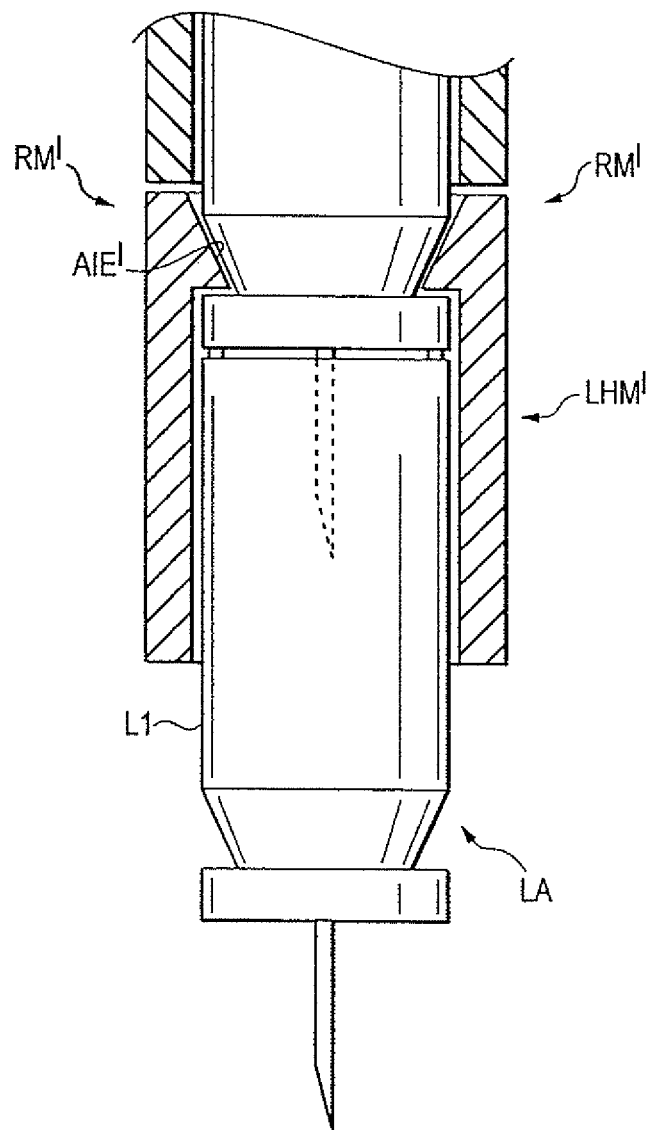
FIG. 14 shows a cross-section of an end portion of another embodiment of a lancet holding member which can be used with the multi-lancet unit.
Figure 15:
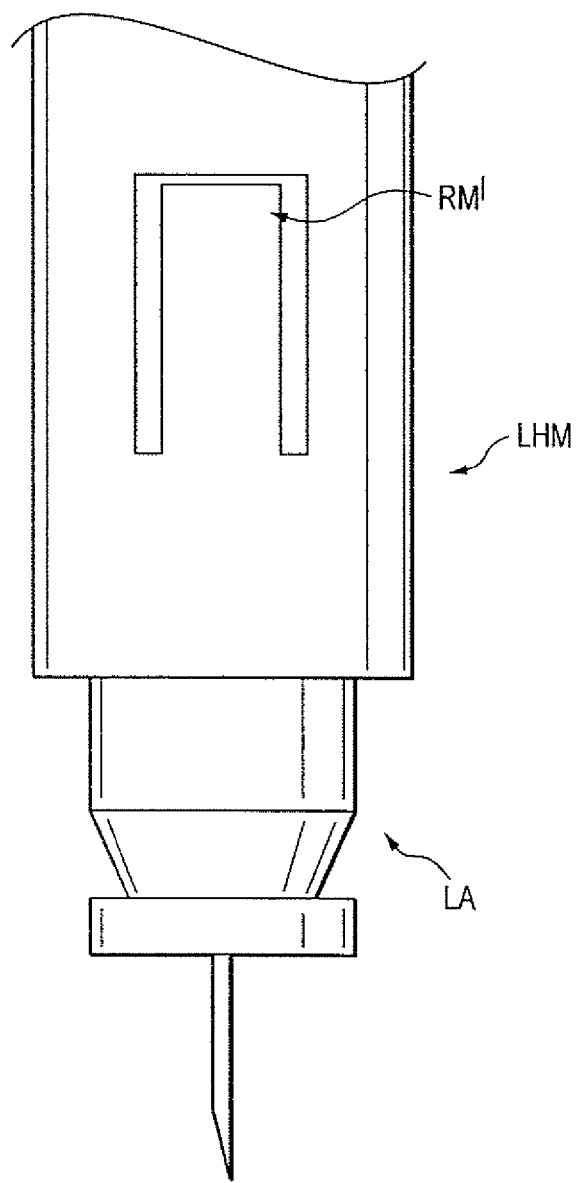
FIG. 15 shows a side view of FIG. 14 rotated 90 degrees.
Figure 16:
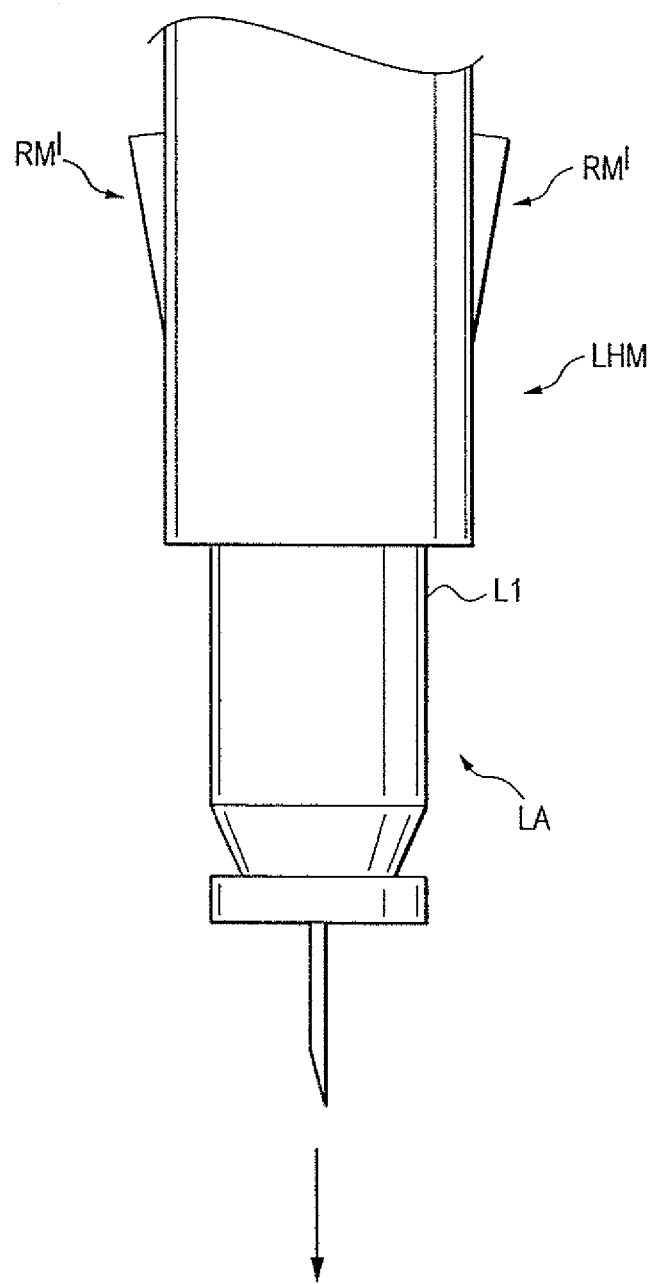
FIG. 16 shows a side view of FIG. 14 and illustrates deflection of the retaining members while the multi-lancet unit advances forward and out of the lancet holding member.
Figure 17:
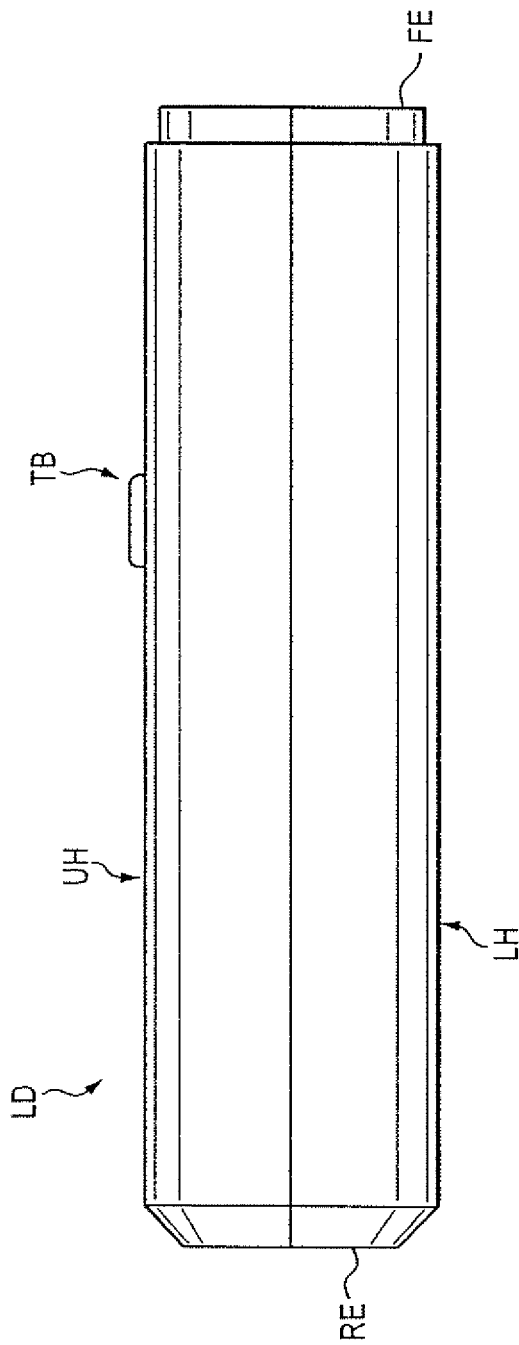
FIG. 17 shows a side view of one embodiment of a lancet device which can include the multi-lancet unit and the lancet holding member shown above.

FIGS. 14-16 illustrate another non-limiting way in which the unit LA can be mounted to a lancet holding member LHM' of a lancet device. Examples of lancet devices which can use the lancet holding member LHM' are disclosed in the following documents: U.S. Pat. No. 6,811,557 to SCHRAGA, U.S. Pat. No. 6,530,937 to SCHRAGA, U.S. Pat. No. 6,346,114 to SCHRAGA, U.S. Pat. No. 6,190,398 to SCHRAGA, U.S. Pat. No. 6,156,051 to SCHRAGA, U.S. Pat. No. 6,022,366 to SCHRAGA, U.S. Pat. No. 5,908,434 to SCHRAGA, U.S. Pat. No. 5,797,942 to SCHRAGA, U.S. Pat. No. 5,628,764 to SCHRAGA, U.S. Pat. No. 5,464,418 to SCHRAGA, and U.S. Pat. No. 5,613,978 to HARDING, the disclosures of which are hereby expressly incorporated by reference in their entireties.

Again with reference to FIGS. 14-16, it can be seen that the lancet holding member LHM' has a front end from which a lancet L1 extends and through which the unit LA moves through. In order to ensure that the unit LA advances and/or indexes out of the front end one lancet at a time, the lancet holding member LHM' includes oppositely arranged retaining members or mechanisms RM'. In the embodiment shown in FIGS. 14-16, the retaining mechanisms RM' are integrally formed with the lancet holding member LHM' (see FIG. 15). The retaining mechanisms RM' are arranged on the front end of the lancet holding member LHM' and are capable of deflecting outwards when the unit LA is moved outwardly (see FIG. 16). The retaining members RM' include tapered and/or angled inner edges AIE' which utilize an angle which is generally complementary to that of the retaining recesses LR (see FIG. 14). As can be seen when comparing FIGS. 14 and 16, the retaining members RM' are made of a resilient or spring-like material which can be deflected outwards (see FIG. 16) when the unit LA is moved out of the front end of the lancet holding member LHM'. The angles of the edge AIE' and the recess LR are such that they facilitate outward deflection of the retaining members RM' when the unit LA is moved in the direction shown in FIG. 16. However, because the retaining members RM' have the properties of a natural spring, when the unit LA is advanced out by the length of a lancet, the edges AIE' again engage with another retaining recess LR thereby locking the unit LA in the next position.

FIGS. 17-21 illustrate one non-limiting preferred embodiment of a unit LA and a lancet device LD which can utilize the unit LA. The lancet device LD utilizes a two part body made of an upper housing UH and a lower housing LH which can be connected to each other by, e.g., snap connection, adhesive bonding, or ultrasonic welding. The housing parts UH and LH can be made of the same conventional materials as are used in conventional lancet devices and are preferably made of synthetic resin. A trigger button TB is mounted to the body and functions to cause the lancet holding member LHM to move to an extended position when it is activated. Examples of lancet devices which can use similar trigger buttons are disclosed in the following documents: U.S. Pat. No. 6,811,557 to SCHRAGA, U.S. Pat. No. 6,346,114 to SCHRAGA, U.S. Pat. No. 6,156,051 to SCHRAGA, U.S. Pat. No. 5,908,434 to SCHRAGA, U.S. Pat. No. 5,797,942 to SCHRAGA, U.S. Pat. No. 5,628,764 to SCHRAGA, U.S. Pat. No. 5,464,418 to SCHRAGA, and U.S. Pat. No. 5,613,978 to HARDING, the disclosures of which are hereby expressly incorporated by reference in their entireties.

Figure 18:
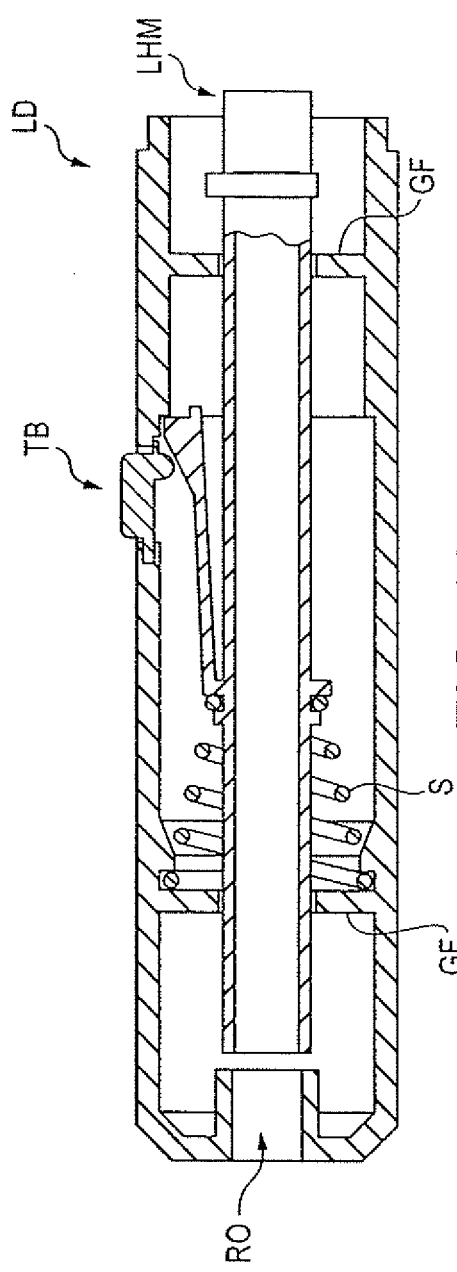
FIG. 18 shows a cross-section view of the lancet device shown in FIG. 17.
Figure 19:
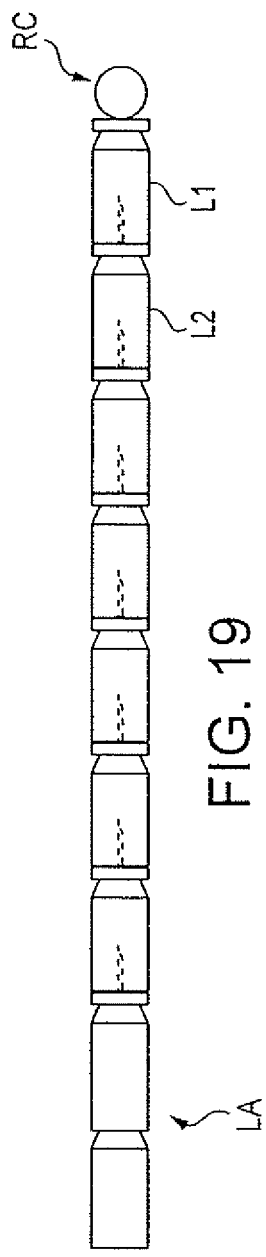
FIG. 19 shows a side view of another embodiment of a multi-lancet unit which can be used on the lancet device shown in FIGS. 17 and 18.
Figure 20:
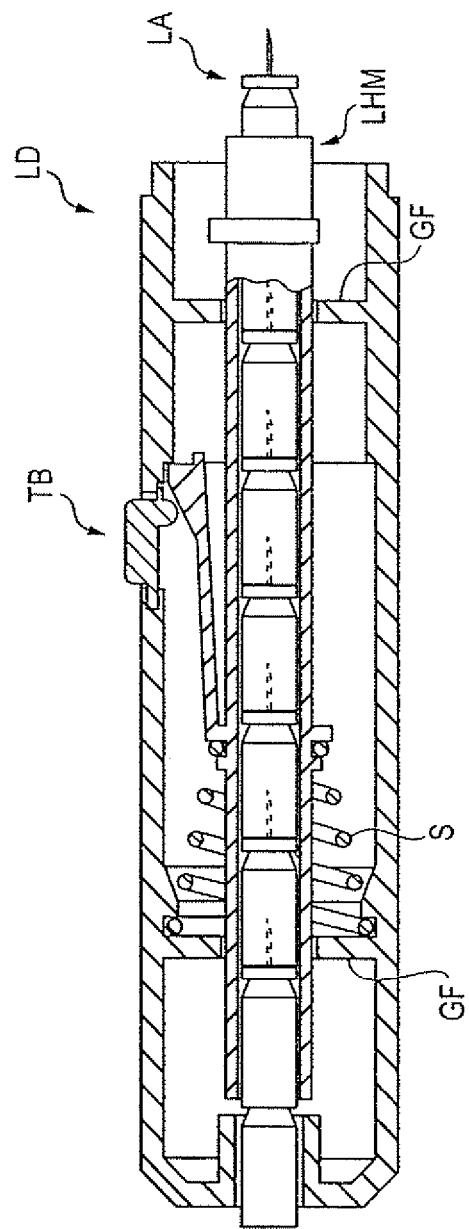
FIG. 20 shows the multi-lancet unit of FIG. 19 installed within the lancet device shown in FIGS. 17 and 18. The lancet device is shown in the armed/trigger set position.
Figure 21:
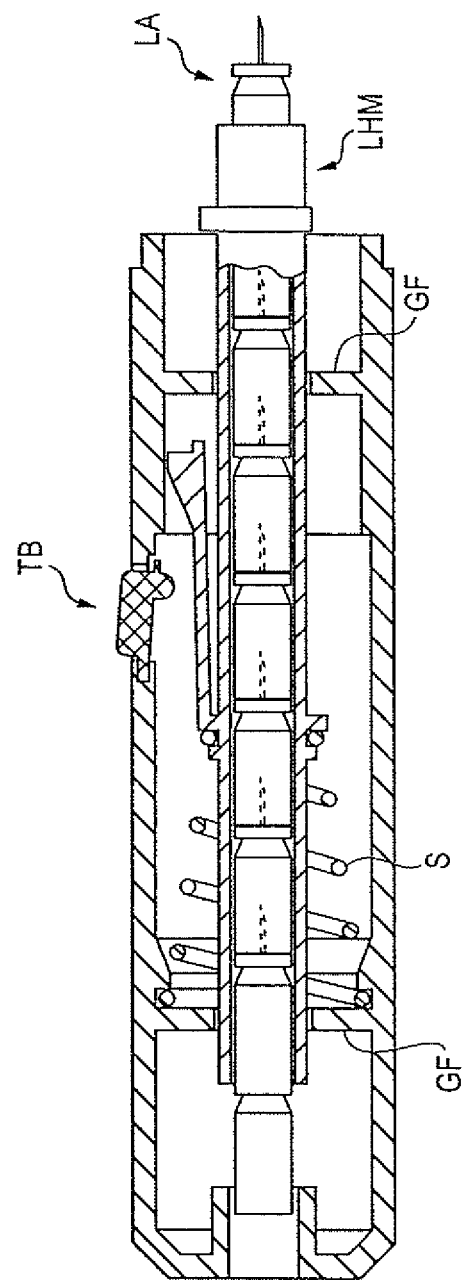
FIG. 21 shows the multi-lancet unit of FIG. 19 installed within the lancet device shown in FIGS. 17 and 18. The lancet device is shown in the extended/triggered position.

As can be seen when comparing FIGS. 18 and 20, the lancet holding member LHM of the lancet device LD is hollow and/or tubular and is sized to receive therein the unit LA. The lancet device LD has a rear opening RO which is aligned with the opening of the lancet holding member LHM. This opening RO allows the user to insert that unit shown in FIG. 19 into the lancet holding member LHM from the rear end of the lancet device LD. Once installed therein (see FIG. 20), the protective cap RC can be removed. After the tip is installed (not shown) on the lancet device LD, the lancet device LD will then be ready for use in pricking a user's skin. After use, the user simply removes the tip, pulls on the used lancet L1 until the unit LA advances to the next lancet L2. The user will then be able to break off the used lancet (see e.g., FIGS. 12 and 13) thereby exposing the next new lancet L2. The lancet device LD will then be ready for use once again after replacement of the tip on the lancet device LD. FIG. 21 shows how the lancet holding member LHM moves to the extended position under the action of the spring S once the trigger button TB is activated. In order to ensure that the lancet holding member LHM is guided within the lancet device LD in a generally linear manner without also rotating to a significant extent, the lancet device LD uses two or more spaced apart guiding flanges GF. In order to ensure that the spring S also biases the lancet holding member LHM back into the lancet device LD after it has moved to the extended position, the spring S has one end coupled to the body and another end coupled to the lancet holding member LHM. Since the use of springs and trigger buttons, as well as the interaction of the trigger button with the lancet holding member, on lancet devices is well know, the details of such devices and arrangements will not be discussed in detail herein.

Figure 22:
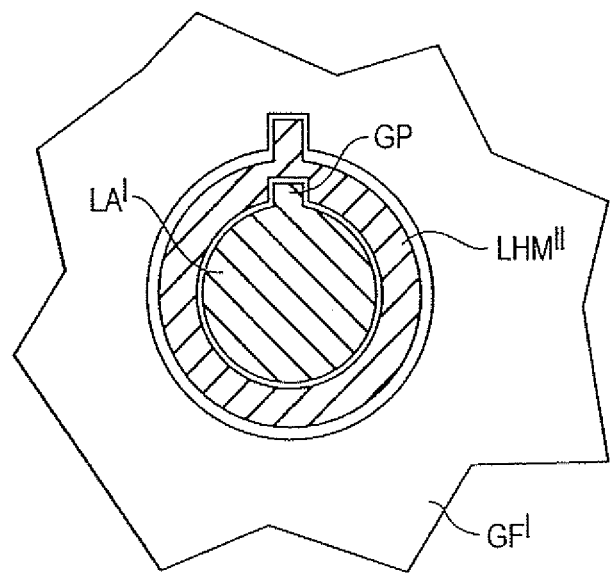
FIG. 22 shows a partial end view of another embodiment of the lancet device, lancet holding member, and multi-lancet unit. This embodiment is similar to that of FIGS. 20 and 21 except that the lancets, the lancet holding member and guide flanges of the lancet device include arrangements for linearly and non-rotatably guiding movement of the holding member within the lancet device and for linearly and non-rotatably guiding movement of the multi-lancet unit within the lancet holding member.
Figure 24:
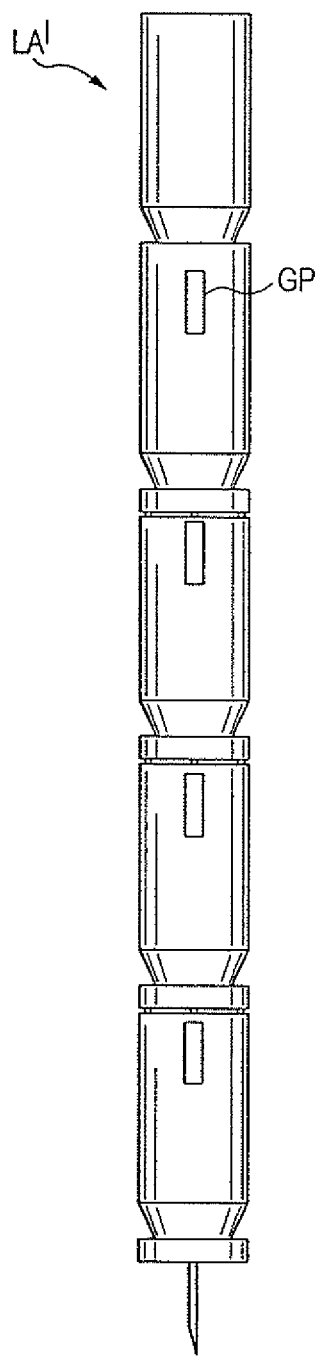
FIG. 24 shows a side view of one embodiment of the multi-lancet unit which can be used in the lancet devices shown in FIGS. 22 and 23.
Figure 25:
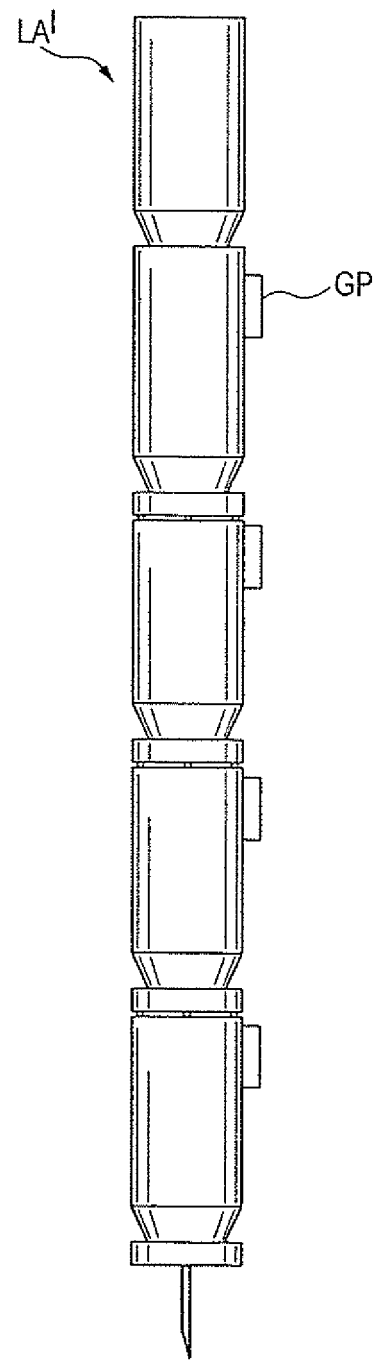
FIG. 25 shows a side view similar to that of FIG. 24 rotated 90 degrees.

FIG. 22 illustrates one non-limiting optional configuration in order to ensure that the lancet holding member LHM" of the lancet device LD is linearly guided within the lancet device LD without rotating. The arrangement uses an elongated guiding projection that is integrally formed with the lancet holding member LHM" and which acts to linearly guide the movement of the lancet holding member LHM"

within the lancet device LD by engaging with grooves arranged on the guiding flanges GF'. The arrangement also uses guiding projections GP integrally formed with the lancets (see FIGS. 24 and 25). The projections GP act to linearly guide the movement of the unit LA' within the lancet holding member LHM" when the unit LA' is advanced between positions. As is evident from FIG. 22, the projections GP slide within a groove formed in an inside cylindrical surface of the lancet holding member LHM".

Figure 23:
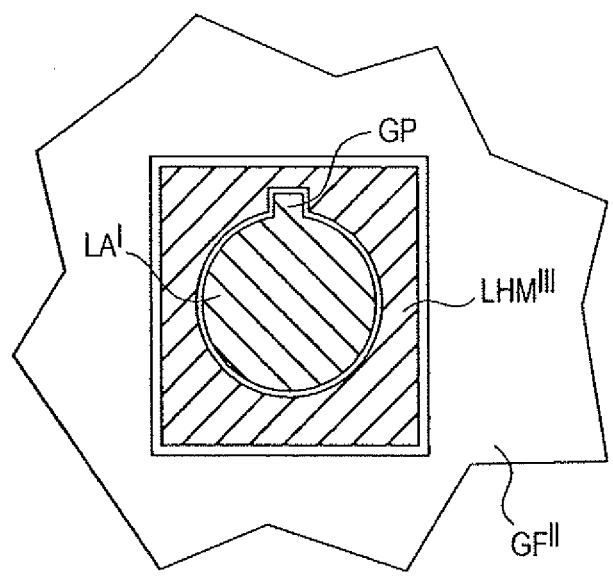
FIG. 23 shows a partial end view of another embodiment of the lancet device, lancet holding member, and multi-lancet unit. This embodiment is similar to that of FIGS. 20 and 21 except that the lancets, the lancet holding member and guide flanges of the lancet device include arrangements and/or an external shape for linearly and non-rotatably guiding movement of the holding member within the lancet device and for linearly and non-rotatably guiding movement of the multi-lancet unit within the lancet holding member.

FIG. 23 illustrates another non-limiting optional configuration in order to ensure that the lancet holding member LHM''' of the lancet device LD is linearly guided within the lancet device LD without rotating. The arrangement uses a polygonal-shaped, e.g., square or rectangular, lancet holding member LHM''', which moves within a slightly larger but correspondingly shaped openings in the guiding flanges GF''. The arrangement also uses guiding projections GP integrally formed with the lancets (see FIGS. 24 and 25). The projections GP act to linearly guide the movement of the unit LA' within the lancet holding member LHM''' when the unit LA' is advanced between positions. As is evident from FIG. 23, the projections GP slide within a groove formed in an inside cylindrical surface of the lancet holding member LHM'''.

Figure 26:
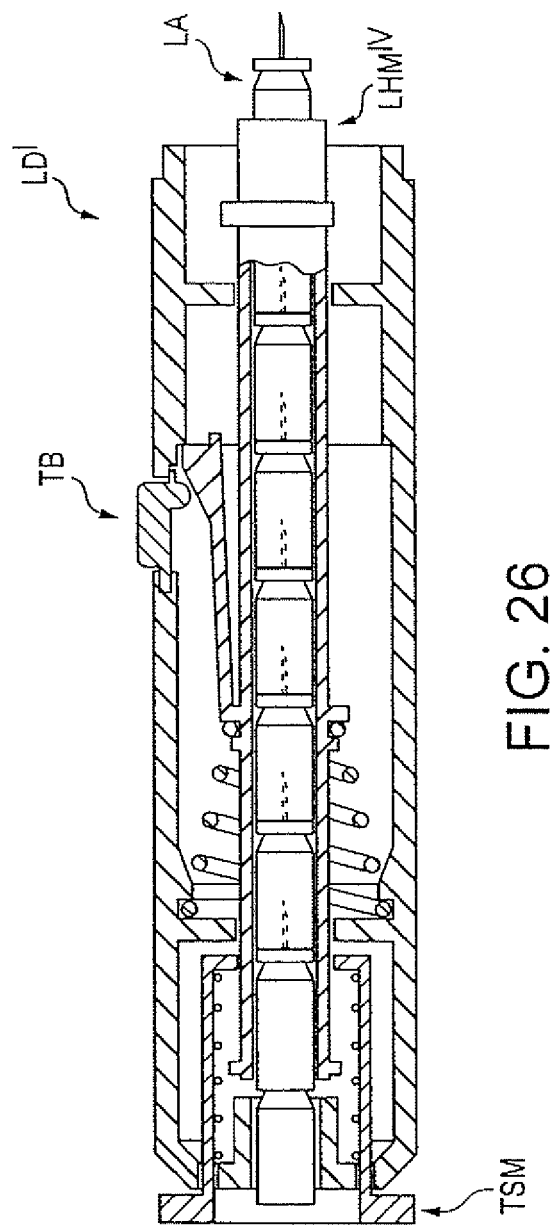
FIG. 26 shows another embodiment of a lancet device which can utilize the multi-lancet unit described above. This device is similar to that shown in FIGS. 20 and 21 except that it additionally includes a mechanism for re-setting and/or moving the lancet holding member back into the trigger set/armed position.

FIG. 26 illustrate another non-limiting preferred embodiment of a unit LA and a lancet device LD' which can utilize the unit LA. The lancet device LD' is similar to that shown in FIGS. 17, 19, 20 and 21 except that it also includes a trigger setting mechanism TSM. The lancet holding member LHM$^{IV}$ is similar to the one used in the embodiment shown in FIGS. 17, 19, 20 and 21 except that the rear end portion includes a flange which can be gripped and/or engages by the trigger setting mechanism TSM. The use of such mechanisms on lancet devices are well know and the invention is not limited to any particular type of trigger setting mechanism. Examples of lancet devices which can use similar trigger setting arrangements are disclosed in the following documents: U.S. Pat. No. 6,156,051 to SCHRAGA and U.S. Pat. No. 6,022,366 to SCHRAGA, the disclosures of which are hereby expressly incorporated by reference in their entireties.

Figure 27:
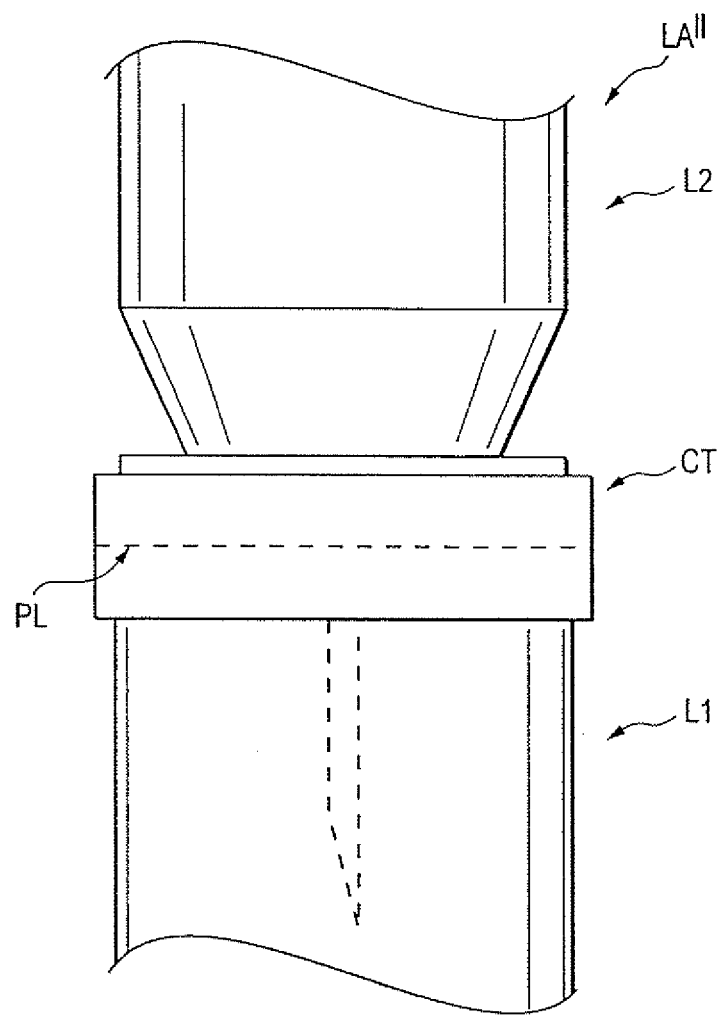
FIG. 27 shows another non-limiting way in which the lancets can be removably connected to each other. In this Figure, a single wrap of connecting tape is used to connect two adjacent lancets.

FIG. 27 illustrate another non-limiting way in which the lancets can be connected instead of and/or in addition to the connecting members CM. In this embodiment, the lancets of the unit LA" are connected with one or more wraps of connecting tape CT which includes a breakable perforation line PL in order to allow the user to separate the lancets from each other. The connecting tape CT preferably is sufficiently thin so as not to cause the unit LA" to become stuck within the lancet holding member LHM.

Figure 28:
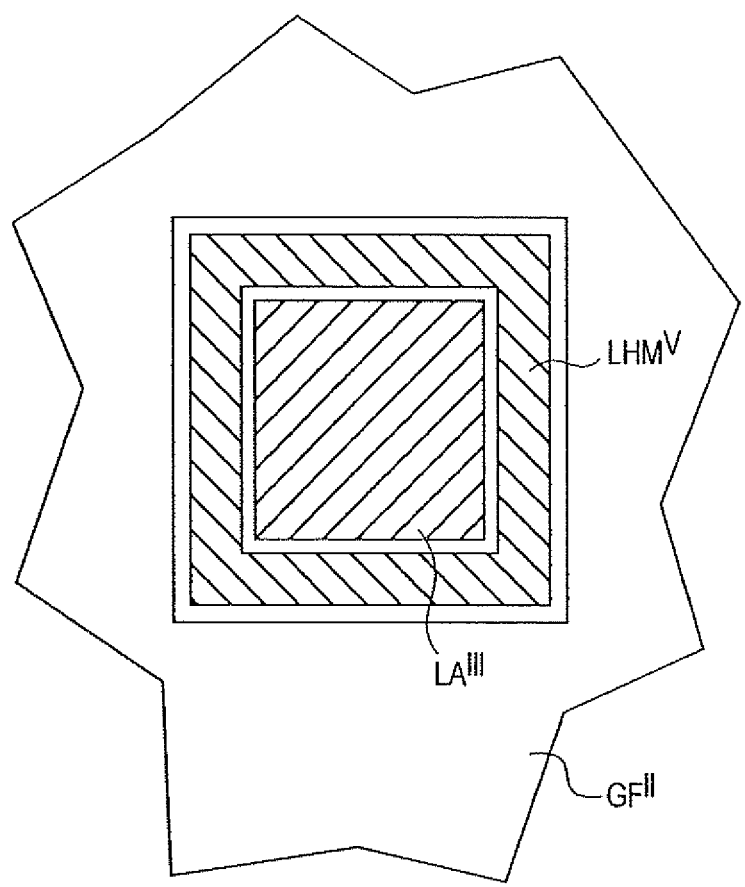
FIG. 28 shows a partial end view of another embodiment of the lancet device, lancet holding member, and multi-lancet unit. This embodiment is similar to that of FIGS. 20 and 21 except that the lancets, the lancet holding member and guide flanges of the lancet device include arrangements and/or an external shape for linearly and non-rotatably guiding movement of the holding member within the lancet device and for linearly and non-rotatably guiding movement of the multi-lancet unit within the lancet holding member.

FIG. 28 illustrates another non-limiting optional configuration in order to ensure that the lancet holding member LHM$^{IV}$ of the lancet device LD is linearly guided within the lancet device LU) without rotating. The arrangement uses a polygonal-shaped, e.g., square or rectangular, lancet holding member LHM$^{IV}$ which moves within a slightly larger but correspondingly shaped opening in the guiding flanges GF". The arrangement also uses a polygonal-shaped, e.g., square or rectangular, unit LA''' which moves with a slightly larger but correspondingly shaped openings in the lancet holding member LHM$^{IV}$.

FIGS. 29 and 30 illustrate another non-limiting embodiment of a lancet device LD" which uses another embodiment of a lancet holding member LHM$^{V}$. The device is similar to that shown in FIGS. 17, 18, 20 and 21 except that it also includes a lancet advancing system LAS. The system LAS includes s slot formed on the lancet device body, a slot formed in the lancet holding member LHM$^{V}$, and a push-button slide member UAM which is biased by a spring SP and which slides moves inwards to engage one of the retaining recess LR, slides forwardly to cause advancing movement of the unit LHM$^{V}$. The user can then move the member UAM manually back to an initial position in order to engage the unit LA" again. This arrangement for manually moving the unit can be used on any of the lancet device embodiments disclosed herein. Moreover, the invention is not limited to the particular arrangement shown herein and can utilize other arrangements for more safely advancing the unit within the lancet holding member.

Figure 32:
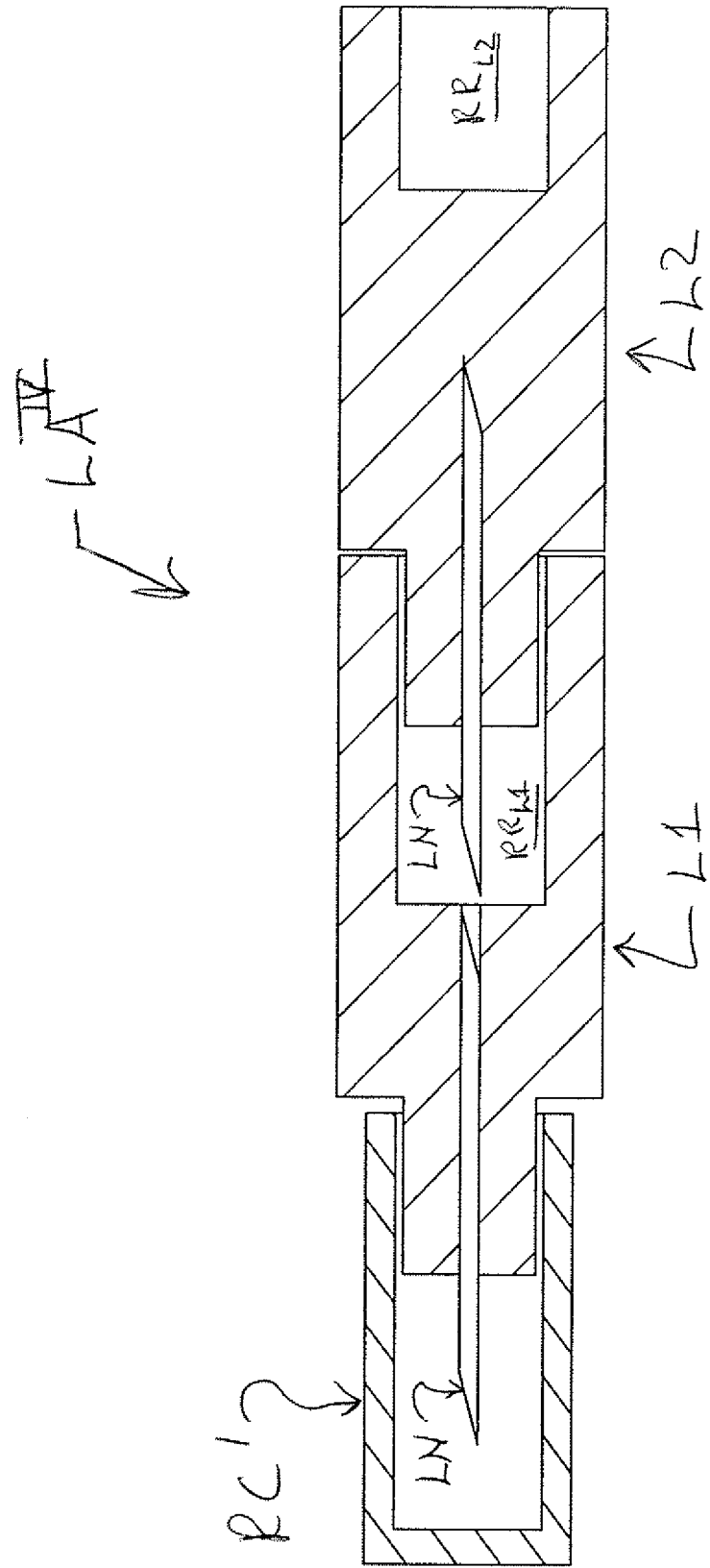
FIG. 32 shows a cross-section view of another embodiment of the multi-lancet unit. This embodiment utilizes two or more lancets which each have a front projecting portion and a rear recess portion. A cap is removably connected to the front projecting portion of the first lancet.
Figure 36:
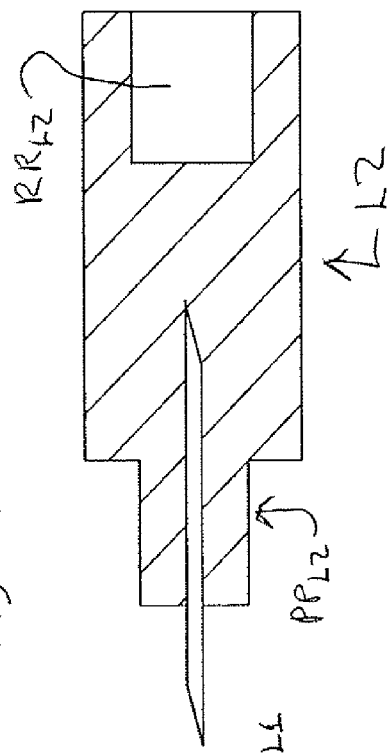
FIG. 36 shows a cross-section view of the front lancet of the multi-lancet unit shown in FIG. 32 and after the multi-lancet unit is used to puncture the skin of a user and after the front lancet has been separated from the rear lancet.
Figure 37:
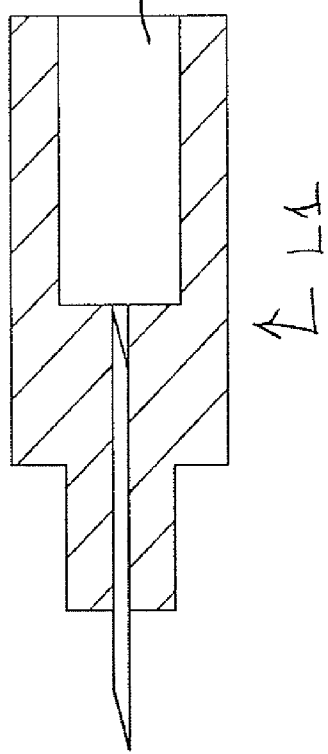
FIG. 37 shows a cross-section view of the rear lancet of the multi-lancet unit shown in FIG. 32 and after the multi-lancet unit is used to puncture the skin of a user and after the front lancet has been separated from the rear lancet.
Figure 38:
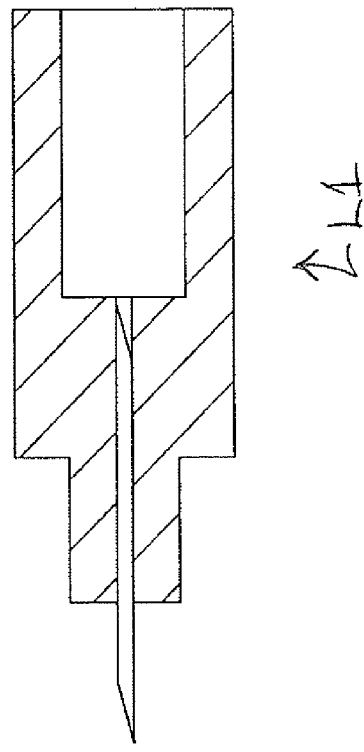
FIG. 38 shows a cross-section view of the rear lancet of the multi-lancet unit shown in FIG. 32 and after the multi-lancet unit is used to puncture the skin of a user and after the front lancet has been separated from the rear lancet and placed in a position behind the rear lancet.
Figure 39:
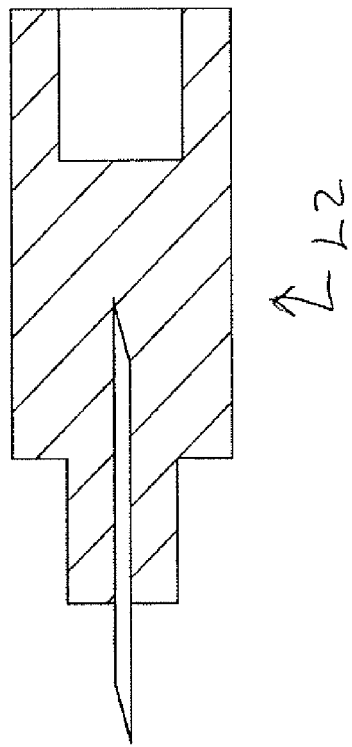
FIG. 39 shows a cross-section view of the front lancet of the multi-lancet unit shown in FIG. 32 and after the multi-lancet unit is used to puncture the skin of a user and after the front lancet has been separated from the rear lancet and placed in a position behind the rear lancet.
Figure 52:
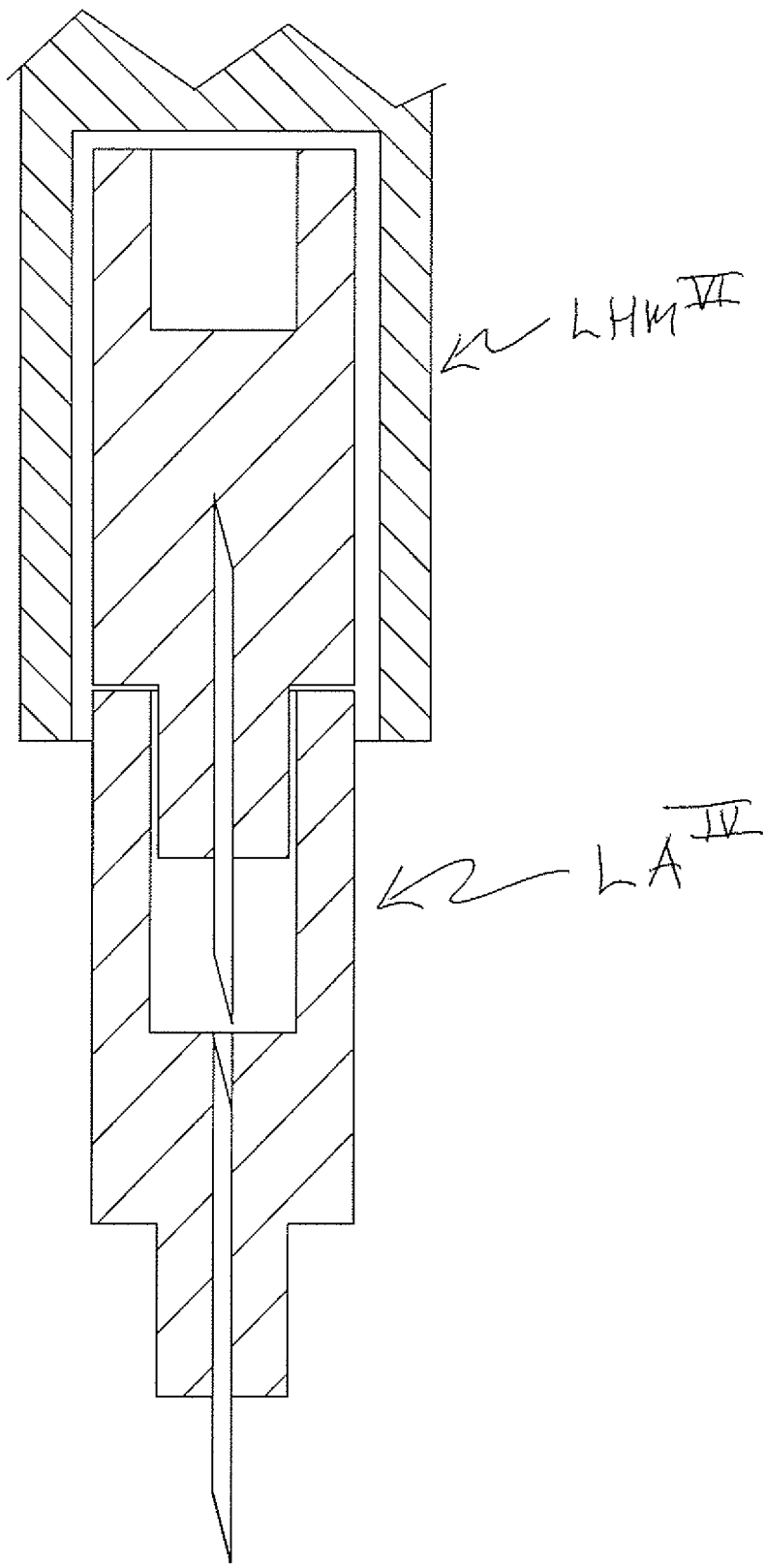
FIG. 52 shows a partial cross-section view of one non-limiting way in which the multi-lancet unit can be positioned within a front receiving portion of a conventional lancet holding member of a lancet device.

FIGS. 32-41 show another embodiment of the multi-lancet unit LA$^{IV}$. This embodiment utilizes two or more lancets L1 and L2 arranged one in front of the other. The front lancet L1 has a generally cylindrical body which includes a front projecting portion $PP_{L1}$ from which a lancet needle LN extends and a rear recess portion $RR_{L1}$. The rear lancet L2 also has a generally cylindrical body which includes a front projecting portion $PP_{L2}$ from which a lancet needle LN extends and a rear recess portion $RR_{L2}$. As is shown in FIG. 32, the rear recess portion $RR_{L2}$ of the rear lancet L2 has a shorter axial length than the rear recess portion $RR_{L1}$ of the front lancet L1. As is shown in FIG. 40, this arrangement allows the lancet needle LN of the front lancet L1 to be forced into a retracted position when the front projecting portion $PP_{L1}$ of the front lancet L1 is positioned in the rear recess portion $RR_{L2}$. The advantage of this feature is that the user will not be able to inadvertently use the lancet unit LA$^{IV}$ more than twice. In order to protect the user from being accidentally injured, e.g. when the user initially inserts the lancet unit LA$^{IV}$ into a holding member of a lancet device (see e.g., FIG. 52), a cap RC' is removably connected the from front projecting portion $PP_{L1}$ of the first lancet L1.

One non-limiting way of using the lancet unit LADS will now be described. As is shown in FIGS. 33 and 34, once installed in a lancet device (not shown), the user can remove the cap RC'. The lancet can now be used to puncture the skin of a user. FIG. 35 shows the multi-lancet unit after the multi-lancet unit LA$^{IV}$ is used to puncture the skin of a user. The needle LN which has been used is shown to have contaminates CT, e.g., blood. As is shown in FIGS. 36-39, the user can now separate the used front lancet L1 from the unused rear lancet L2. Next, the user places the rear lancet L2 in front of the front lancet L1. The user can then force the projecting portion $PP_{L1}$ of the front lancet L1 into the rear recess portion $RR_{L2}$ of the rear lancet L2. This causes the lancet needle LN of the front lancet L1 to retract and essentially renders this lancet unusable again. At this point, the multi-lancet unit LA$^{IV}$ is ready to again be placed in the lancet device and used puncture the skin of a user with a fresh needle, i.e., the needle LN of the rear lancet L2 which has assumed the position of the front lancet. Once used again, the multi-lancet unit LA$^{IV}$ can be fitted with the safety cap RC', and discarded. The lancet unit LA$^{IV}$ now cannot be used again because, if the user tries to place the front lancet L1 back in front of the rear lancet L2, the needle LN of the front lancet L1 will be retracted and the user will therefore have a visual indicator that the unit LA$^{IV}$ has already been used twice (i.e., reached its useful life) and that it is time to use new lancet unit LA$^{IV}$.

FIGS. 42-49 show another embodiment of the multi-lancet unit LA$^{V}$. This embodiment also utilizes two or more lancets L1 and L2 arranged one in front of the other. The front lancet L1 has a generally cylindrical body which includes a front projecting portion $PP_{L1}$ from which a lancet needle LN extends and a rear recess portion $RR_{L1}$. The rear lancet L2 also has a generally cylindrical body which includes a front projecting portion $PP_{L2}$ from which a lancet needle LN extends and a rear recess portion $RR_{L2}$. As is shown in FIG.

Figure 49:
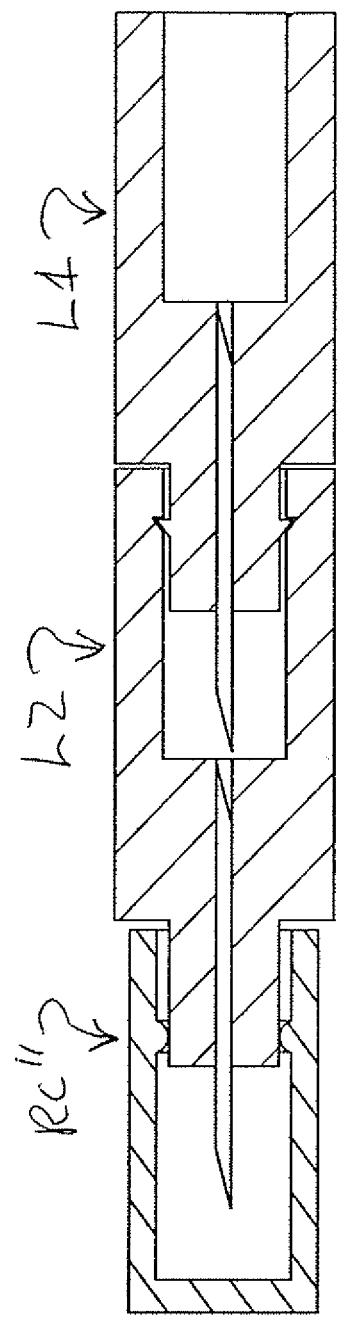
FIG. 49 shows a cross-section view of the multi-lancet unit after it has been used a second time to puncture the skin of a user. The cap is now removably connected the rear lancet which has become the front lancet.

42, unlike the previous embodiment, the rear recess portion $RR_{L2}$ of the rear lancet L2 has substantially the same axial length as the rear recess portion $RR_{L1}$ of the front lancet L1. As is shown in FIG. 49, this arrangement allows the front projecting portion $PP_{L1}$ of the front lancet L1 to be locked within the rear recess portion $RR_{L2}$ of the rear lancet L2. The advantage of this feature is that the user will not be able to inadvertently use the lancet unit $LA^V$ more than twice. In order to protect the user from being accidentally injured, e.g. when the user initially inserts the lancet unit $LA^V$ into a holding member of a lancet device (see e.g., FIG. 52), a cap RC" is removably connected the from front projecting portion $PP_{L1}$ of the first lancet L1.

Figure 47:
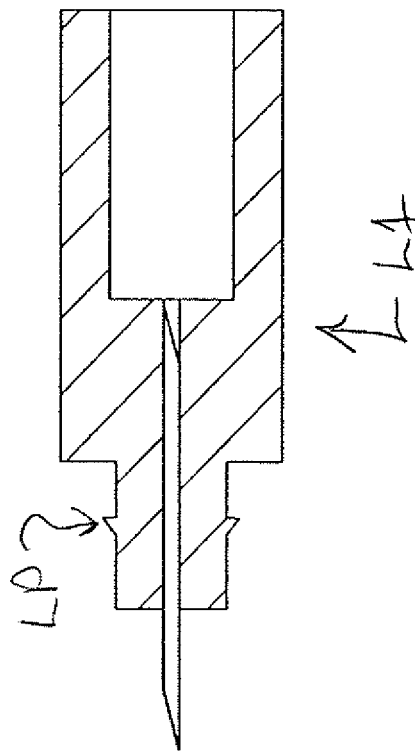
FIG. 47 shows a cross-section view of the rear lancet of the multi-lancet unit shown in FIG. 42 and after the multi-lancet unit is used to puncture the skin of a user and after the front lancet has been separated from the rear lancet and placed in a position behind the rear lancet.
Figure 48:
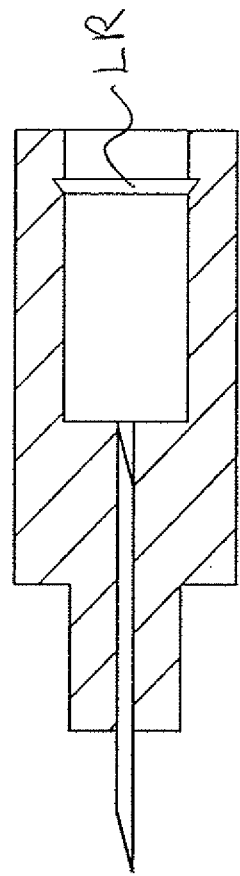
FIG. 48 shows a cross-section view of the front lancet of the multi-lancet unit shown in FIG. 42 and after the multi-lancet unit is used to puncture the skin of a user and after the front lancet has been separated from the rear lancet and placed in a position behind the rear lancet.

One non-limiting way of using the lancet unit $LA^V$ will now be described. As is shown in FIGS. 43 and 44, once installed in a lancet device (not shown), the user can remove the cap RC". The lancet can now be used to puncture the skin of a user. FIGS. 45-46 shows the multi-lancet unit after the multi-lancet unit $LA^V$ is used to puncture the skin of a user. The user can then separate the used front lancet L1 from the unused rear lancet L2. Next, as shown in FIGS. 47 and 48, the user places the rear lancet L2 in front of the front lancet L1. The user can then force the projecting portion $PP_{L1}$ of the front lancet L1 into the rear recess portion $RR_{L2}$ of the rear lancet L2. This causes a locking projection LP of the front lancet L1 to lock with a locking recess LR of the rear lancet L2. At this point, the multi-lancet unit $LA^V$ is ready to again be placed in the lancet device and used puncture the skin of a user with a fresh needle, i.e., the needle LN of the rear lancet L2 which has assumed the position of the front lancet. Once used again, the multi-lancet unit $LA^V$ can be fitted with the safety cap RC', and discarded. The lancet unit $LA^V$ now cannot be used again because the user is prevented by the locking arrangement from placing the front lancet L1 back in front of the rear lancet L2 and the user will therefore have a visual indicator that the unit $LA^V$ has already been used twice (i.e., reached its useful life) and that it is time to use new lancet unit $LA^V$.

Figure 50:
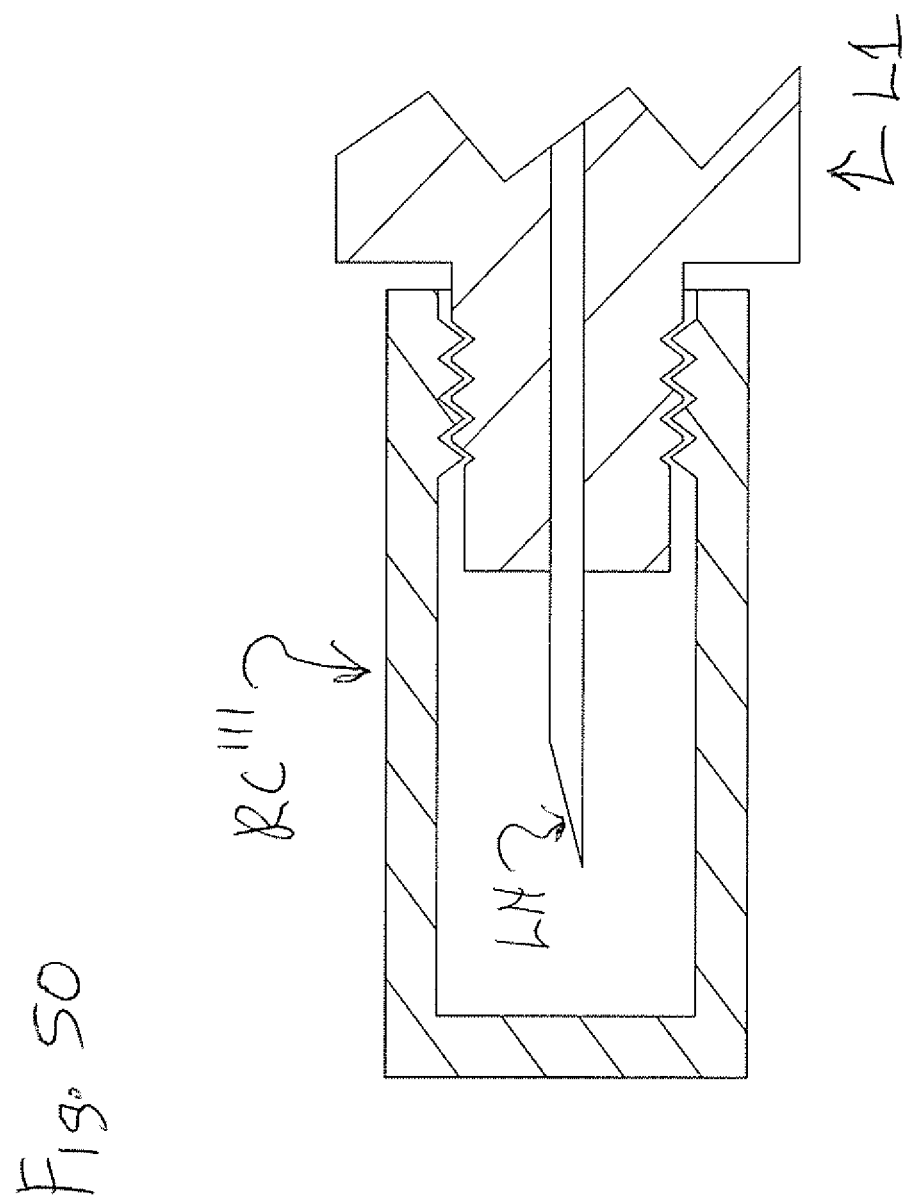
FIG. 50 shows a partial cross-section view of one non-limiting way in which the cap of the above-noted embodiments can be connected to the front projecting portion of the front lancet or rear lancet. The cap is shown threadably connected to the front projecting portion of the front lancet.
Figure 51:
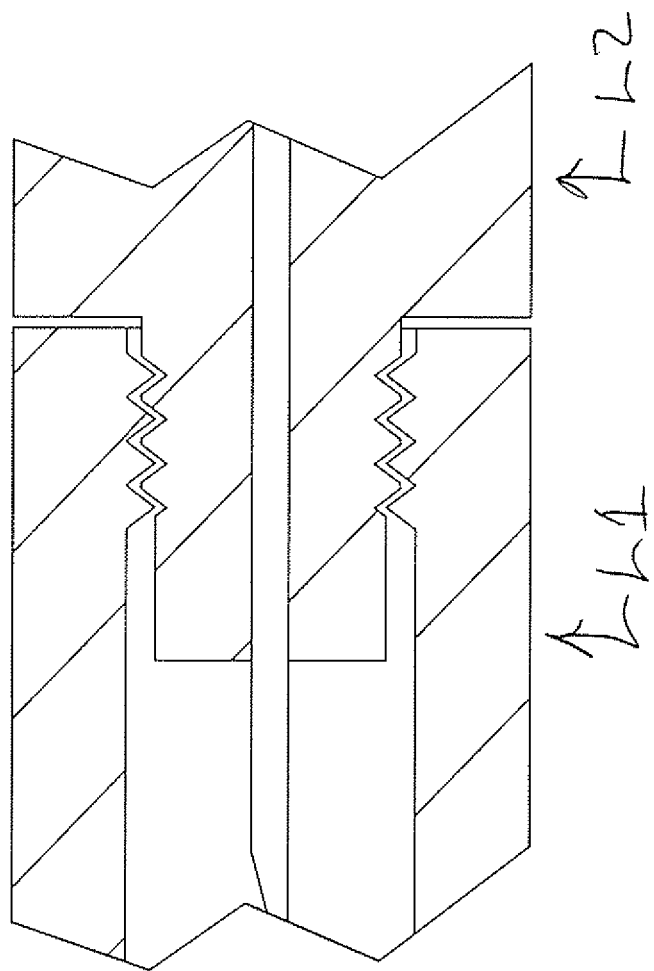
FIG. 51 shows a partial cross-section view of one non-limiting way in which the front and rear lancets can be connected to each other. The front projecting portion of the rear lancet is shown threadably connected to the rear recess portion of the front lancet.

FIG. 50 shows one non-limiting way in which a cap $RC^{III}$ of the above-noted embodiments can be connected to the front projecting portion $PP_{L1}$ of the front lancet L1 or the front projecting portion $PP_{L2}$ of the rear lancet L2. The cap $RC^{III}$ is shown threadably connected to the front projecting portion $PP_{L1}$ of the front lancet L1. FIG. 51 shows one non-limiting way in which the front and rear lancets L1 and L1 can be connected to each other. The front projecting portion $PP_{L2}$ of the rear lancet L2 is shown threadably connected to the rear recess portion $RR_{L1}$ of the front lancet L1.

FIGS. 53-54 show another embodiment of the multi-lancet unit $LA^{VI}$. This embodiment also utilizes two or more lancets L1 and L2 arranged one in front of the other. The front lancet L1 has a generally cylindrical body which includes a front projecting portion $PP_{L1}$ from which a lancet needle LN extends and a rear recess portion $RR_{L1}$. The rear lancet L2 also has a generally cylindrical body which includes a front projecting portion $PP_{L2}$ from which a lancet needle LN extends and a rear recess portion $RR_{L2}$. As is shown in FIG. 53, the rear recess portion $RR_{L2}$ of the rear lancet L2 has a shorter axial length as the rear recess portion $RR_{L1}$ of the front lancet L1 As is shown in FIG. 54, this arrangement allows the lancet needle LN of the front lancet L1 to be forced into a retracted position when the front projecting portion $PP_{L1}$ of the front lancet L1 is positioned in the rear recess portion $RR_{L2}$. In order to protect the user from being accidentally injured, e.g. when the user initially inserts the lancet unit $LA^{VI}$ into a holding member of a lancet device (see e.g., FIG. 52), a cap $RC^{IV}$ is removably connected the from front projecting portion $PP_{L1}$ of the first lancet L1. However, once the user places the cap $RC^{IV}$ on the lancet unit after it is used a second time, the cap $RC^{IV}$ becomes non-removably connected the from front projecting portion $PP_{L2}$ of the rear lancet L2. The advantage of this feature is that the user will not be able to inadvertently use the lancet unit $LA^{VI}$ more than twice.

One non-limiting way of using the lancet unit $LA^{VI}$ will now be described. Once installed in a lancet device (not shown), the user can remove the cap $RC^{IV}$. The lancet can now be used to puncture the skin of a user. The user can then separate the used front lancet L1 from the unused rear lancet L2. Next, the user places the rear lancet L2 in front of the front lancet L1. The user can then force the projecting portion $PP_{L1}$ of the front lancet L1 into the rear recess portion $RR_{L2}$ of the rear lancet L2. This causes the lancet needle LN to retract as in the embodiment shown in FIG. 32. At this point, the multi-lancet unit $LA^{VI}$ is ready to again be placed in the lancet device and used puncture the skin of a user with a fresh needle, i.e., the needle LN of the rear lancet L2 which has assumed the position of the front lancet. Once used again, the multi-lancet unit $LA^{VI}$ can be fitted with the safety cap $RC^{IV}$, and discarded. The lancet unit $LA^{VI}$ now cannot be used again because the user is prevented by the locking engagement of a locking ring and a locking recess from removing the cap $RC^{IV}$ from the rear lancet L2. The user will therefore have a visual indicator that the unit $LA^{VI}$ has already been used twice (i.e., reached its useful life) and that it is time to use new lancet unit $LA^{VI}$.

FIGS. 55-56 show another embodiment of the multi-lancet unit $LA^{VII}$. This embodiment also utilizes two or more lancets L1 and L2 arranged one in front of the other. The front lancet L1 has a generally cylindrical body which includes a front projecting portion $PP_{L1}$ from which a lancet needle LN extends and a rear recess portion $RR_{L1}$. The rear lancet L2 also has a generally cylindrical body which includes a front projecting portion $PP_{L2}$ from which a lancet needle LN extends and a rear recess portion $RR_{L2}$. The rear recess portion $RR_{L2}$ of the rear lancet L2 has substantially the same axial length as the rear recess portion $RR_{L1}$ of the front lancet L1. The rear recess portion $RR_{L2}$ of the rear lancet L2 has a locking recess which, as is shown in FIG. 56, locks with a lock ring arranged on the front projecting portion $PP_{L1}$ of the front lancet L1. In order to protect the user from being accidentally injured, e.g, when the user initially inserts the lancet unit $LA^{VII}$ into a holding member of a lancet device (see e.g., FIG. 52), a cap $RC^V$ is removably connected the from front projecting portion $PP_{L1}$ of the first lancet L1. However, once the user places the cap $RC^V$ on the lancet unit after it is used a second time, the cap $RC^{IV}$ becomes non-removably connected the from front projecting portion $PP_{L2}$ of the rear lancet L2. The cap $RC^V$ has a locking recess which, as is shown in FIG. 56, locks with a lock ring arranged on the front projecting portion $PP_{L2}$ of the rear lancet L2. The advantage of this feature is that the user will be prevented from again using the lancet unit $LA^{VII}$ more than twice. Furthermore, the lancet unit $LA^{VII}$ can now be safely discarded. Of course, the invention contemplates other locking mechanisms other than a lock ring and a locking recess.

One non-limiting way of using the lancet unit $LA^{VII}$ will now be described. Once installed in a lancet device (not shown), the user can remove the cap $RC^V$. The lancet can now be used to puncture the skin of a user using the needle LN of the front lancet L1. The user can then separate the used front lancet L1 from the unused rear lancet L2. Next, the user places the rear lancet L2 in front of the front lancet L1. This causes the two lancets L1 and L2 to become locked to each other via the locking ring of the projecting portion $PP_{L1}$ of the front lancet L1 becoming locked with the locking recess of the rear recess portion $RR_{L2}$ of the rear lancet L2. At this point, the multi-lancet unit $LA^{VII}$ is ready to again be placed in the lancet device and used puncture the skin of a user with a fresh needle, i.e., the needle LN of the rear lancet L2 which has assumed the position of the front lancet. Once used again, the multi-lancet unit $LA^{VII}$ can be fitted with the safety cap $RC^V$, and discarded. The lancet unit $LAV^{II}$ now cannot be used again because the user is prevented by the locking engagement of a locking ring and a locking recess from removing the cap $RC^V$ from the rear lancet L2. The user will therefore have a visual indicator that the unit $LA^{VII}$ has already been used twice (i.e., reached its useful life) and that it is time to use new lancet unit $LA^{VII}$.

The invention also contemplates a lancet unit which uses the locking system of the embodiment shown in FIG. 32 with the cap locking system used in the embodiment shown in FIGS. 53-54. Still further, the invention contemplates using two lancets labeled A and B of 1 and 2 with the front lancet L1 having the letter A or number 1 and the rear lancet L2 having the letter B or number 2. Once the lancet unit is used to puncture the skin of a user, the user can then separate the used front lancet L1 from the unused rear lancet L2. Next, the user places the rear lancet L2 in front of the front lancet L1. The user now know that he has already used the unit twice because the lancet labeled 2 or B is arranged in front of the lance labeled 1 or A. This feature can also be used on any of the above-noted embodiments to provide additional visual indicators. The two lancets can also be made of different colors. The cap will have the same color as the front lancet so that when the cap is placed on the rear lancet, it will indicate that the unit has already been used twice. This feature also can be used on any of the above-noted embodiments to provide additional visual indicators.

The lancet devices can preferably made transparent and/or translucent so that a user will clearly be able to see the inner workings of the device and note how much of the unit has already been utilized. Of course, the invention is not limited to a body design which is transparent and/or translucent.

All the parts of the lancet device, with the exception of the springs and needles (which can respectively be made of spring steel and stainless steel), may be made from plastic materials and can be formed using conventional injection molding techniques or other known manufacturing methods. However, when practical, other materials and manufacturing processes may also be utilized. In each of the disclosed embodiments, the lancets which make up the multi-lancet unit can be formed individually (e.g., by injection molding) and then connected together as described above. However, the invention also contemplates forming the multi-lancet unit (e.g., by injection molding) as a one-piece member. In this latter case, the lancet needles can be placed (e.g., at predetermined locations) within the mold(s) which will form the multi-lancet unit. Then, the mold(s) is filled with the melted plastic material. Of course, provision is made in the mold(s) for producing the breakable connections will allow the lancets to be separated from the unit.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A multi-lancet unit in combination with a lancet device, the combination comprising:
    a plurality of lancets arranged one in front of the other;
    a holding member receiving therein the multi-lancet unit;
    the holding member being movable at least between a trigger-set position and a puncturing position;
    a mechanism structured and arranged to move the multi-lancet unit within the holding member; and
    each lancet comprising a front end, a needle which extends from the front end, and a rear end,
    wherein the front end of at least one of the plurality lancets is removably connected to the rear end of another of the plurality of lancets.

2. The combination of claim 1, wherein the plurality of lancets comprises two lancets.

3. The combination of claim 1, wherein the plurality of lancets comprises at least three lancets.

4. The combination of claim 1, wherein the plurality of lancets is between five lancets and twenty lancets.

5. The combination of claim 1, wherein the plurality of lancets is between eight lancets and twelve lancets.

6. The combination of claim 1, wherein each of the plurality of lancets comprises a generally cylindrical portion.

7. The combination of claim 1, wherein each of the plurality of lancets comprises a non-circular cross-section when viewed perpendicular to a center axis of the plurality of lancets.

8. The combination of claim 1, wherein at least one of the plurality of lancets comprises a locking mechanism.

9. The combination of claim 8, wherein the locking mechanism is one of a locking recess and a locking projection.

10. The combination of claim 1, wherein at least one of the plurality of lancets comprises at least one of a locking recess and a locking member.

11. The combination of claim 1, wherein the needle of at least one of the plurality of lancets is retractable.

12. The combination of claim 1, further comprising:
    a depth adjustment mechanism;
    a cocking mechanism; and
    a locking or retaining mechanism arranged on the holding member.

13. A method of puncturing a surface of skin using the lancet device of claim 1, the method comprising:
    arranging the lancet device adjacent against a user's skin; and
    triggering the lancet device so that one of the plurality of lancets is caused to penetrate the user's skin.

14. A method of puncturing a surface of skin using the lancet device of claim 1, the method comprising:
    arranging the lancet device adjacent against a user's skin;
    triggering the lancet device so that one of the plurality of lancets is caused to penetrate the user's skin; and
    after triggering, removing a forward-most lancet.

15. A method of puncturing a surface of skin using the lancet device of claim 1, the method comprising:
    arranging the lancet device adjacent against a user's skin;
    triggering the lancet device so that one of the plurality of lancets is caused to penetrate the user's skin; and after triggering, moving the multi-lancet forwardly using the mechanism.

16. A method of making the multi-lancet unit of claim 1, the method comprising:
    forming each of the plurality of lancets;
    arranging the plurality of lancets in a row to form the multi-lancet unit; and
    inserting the multi-lancet unit into the holding member of the lancet device.

17. A multi-lancet unit in combination with a lancet device, the combination comprising:
    a plurality of lancets arranged in a row;
    a holding member receiving therein the multi-lancet unit;
    the holding member being movable at least between a trigger-set position and a puncturing position;
    a mechanism structured and arranged to move the multi-lancet unit within the holding member between a plurality of predetermined axial positions; and
    each lancet comprising a front end, a needle which extends from the front end, a rear end, an opening extending into the rear end,
    wherein the front end of at least one of the plurality lancets is removably connected to the rear end of another of the plurality of lancets.

18. The combination of claim 17, wherein the plurality of lancets comprises two lancets.

19. The combination of claim 17, wherein the plurality of lancets comprises at least three lancets.

20. The combination of claim 17, wherein the plurality of lancets is between five lancets and twenty lancets.

21. The combination of claim 17, wherein the plurality of lancets is between eight lancets and twelve lancets.

22. The combination of claim 17, wherein each of the plurality of lancets comprises a generally cylindrical portion.

23. The combination of claim 17, wherein each of the plurality of lancets comprises a non-circular cross-section when viewed perpendicular to a center axis of the plurality of lancets.

24. The combination of claim 17, wherein one of the plurality of lancets is configured to be non-removably connected to another of the plurality of lancets.

25. The combination of claim 17, wherein one of the plurality of lancets is configured to be non-removably connected to another of the plurality of lancets after said lancets are separated from each other and connected to each other in a different configuration.

26. The combination of claim 17, further comprising a cap which is configured to be removably connected to one of the plurality of lancets and configured to be non-removably connected to another of the plurality of lancets.

27. The combination of claim 17, further comprising:
    a depth adjustment mechanism;
    a cocking mechanism; and
    a locking or retaining mechanism arranged on the holding member.

28. A method of puncturing a surface of skin using the lancet device of claim 17, the method comprising:
    arranging the lancet device adjacent against a user's skin; and
    triggering the lancet device so that one of the plurality of lancets is caused to penetrate the user's skin.

29. A method of puncturing a surface of skin using the lancet device of claim 17, the method comprising:
    arranging the lancet device adjacent against a user's skin; and
    triggering the lancet device so that one of the plurality of lancets is caused to penetrate the user's skin.

30. A method of puncturing a surface of skin using the lancet device of claim 17, the method comprising:
    arranging the lancet device adjacent against a user's skin;
    triggering the lancet device so that one of the plurality of lancets is caused to penetrate the user's skin; and
    after triggering, moving the multi-lancet forwardly using the mechanism.

31. A method of making the multi-lancet unit of claim 17, the method comprising:
    forming each of the plurality of lancets;
    arranging the plurality of lancets in a row to form the multi-lancet unit; and
    inserting the multi-lancet unit into the holding member of the lancet device.

32. A multi-lancet unit in combination with a lancet device, the combination comprising:
    a plurality of lancets arranged in a row;
    a holding member receiving therein the multi-lancet unit;
    the holding member being movable at least between a trigger-set position and a puncturing position;
    a mechanism structured and arranged to move the multi-lancet unit within the holding member between a plurality of predetermined axial positions;
    the mechanism comprising a portion arranged outside a body of the lancet device and said portion configured to be movable by a user;
    each lancet comprising a front end, a needle which extends from the front end, a rear end, an opening extending axially into the rear end; and
    a cap removably connected to a front one of the plurality of lancets.

33. The combination of claim 32, further comprising:
    a depth adjustment mechanism;
    a cocking mechanism; and
    a locking or retaining mechanism arranged on the holding member.

* * * * *